United States Patent
Bosanac et al.

(10) Patent No.: US 8,895,750 B2
(45) Date of Patent: Nov. 25, 2014

(54) HETEROAROMATIC COMPOUNDS AS BTK INHIBITORS

(71) Applicants: Todd Bosanac, New Milford, CT (US); Michael J. Burke, Newtown, CT (US); Darren Disalvo, New Milford, CT (US); Wang Mao, Milford, CT (US); John Westbrook, Woodbridge, CT (US)

(72) Inventors: Todd Bosanac, New Milford, CT (US); Michael J. Burke, Newtown, CT (US); Darren Disalvo, New Milford, CT (US); Wang Mao, Milford, CT (US); John Westbrook, Woodbridge, CT (US)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 14/209,280

(22) Filed: Mar. 13, 2014

(65) Prior Publication Data

US 2014/0275012 A1    Sep. 18, 2014

Related U.S. Application Data

(60) Provisional application No. 61/782,241, filed on Mar. 14, 2013.

(51) Int. Cl.
| | |
|---|---|
| C07D 417/04 | (2006.01) |
| C07D 417/14 | (2006.01) |
| C07D 487/10 | (2006.01) |
| C07D 487/20 | (2006.01) |
| C07D 487/22 | (2006.01) |
| C07D 487/08 | (2006.01) |
| C07D 277/56 | (2006.01) |

(52) U.S. Cl.
CPC ............ C07D 277/56 (2013.01); C07D 417/04 (2013.01); C07D 487/08 (2013.01); C07D 487/10 (2013.01)
USPC ............. 548/147; 548/194; 544/70; 544/121; 544/364; 544/369; 540/556; 546/16; 546/209; 514/370; 514/326; 514/254.04; 514/249; 514/300; 514/234.5; 514/278; 514/235.8

(58) Field of Classification Search
USPC ................................................. 548/147, 194
See application file for complete search history.

(56) References Cited

U.S. PATENT DOCUMENTS

| | | |
|---|---|---|
| 8,377,946 B1 | 2/2013 | Chen et al. |
| 8,557,803 B2 | 10/2013 | Yamamoto et al. |
| 2008/0076921 A1 | 3/2008 | Honigberg et al. |

FOREIGN PATENT DOCUMENTS

| | | | |
|---|---|---|---|
| CA | 2784647 A1 | * | 7/2011 |
| EP | 2543375 A1 | | 1/2013 |
| WO | 2007117692 A2 | | 10/2007 |
| WO | 2008121742 A2 | | 10/2008 |
| WO | 201012690 A1 | | 2/2010 |
| WO | 2010055304 A2 | | 5/2010 |
| WO | 2011082732 A1 | | 7/2011 |
| WO | 2011152351 A1 | | 12/2011 |
| WO | 2013113097 A1 | | 8/2013 |
| WO | 2014025976 A1 | | 2/2014 |
| WO | 2014068527 A1 | | 5/2014 |
| WO | 2014082598 A1 | | 6/2014 |

OTHER PUBLICATIONS

Abstract in English for WO 2011/082732, publication date Jul. 14, 2011.
Akinleye, A. et al., "Ibrutinib and novel BTK inhibitors in clinical develoopment." Journal of Hematology & Oncology, 2013, 6:59, pp. 1-9.
Chakravarty, S. et al., "Kinase inhibitors: A new tool for the treatment of rheumatoid arthritis." Clinical Immunology, 2013, vol. 148, pp. 66-78.
International Search Report and Written Opinion for PCT/US2013/054096, Sep. 30, 2013.
International Search Report and Written Opinion for PCT/US2014/026113, mailing date Jun. 2, 2014.
International Search Report and Written Opinion for PCT/US2014/026966, mailing date Jul. 22, 2014.
Summary of Pfizer Oral Presentation, "Targeted covalent reversible inhibitors for Bruton's Tyrosine Kinase." Presented by Suvit Thaisrivongs on Apr. 16, 2013.
Whang, J. et al., "Bruton's tyrosine kinase inhibitors for the treatment of rheumatoid arthritis." Drug Discovery Today, 2014, pp. 1-5.

* cited by examiner

*Primary Examiner* — Laura L. Stockton
(74) *Attorney, Agent, or Firm* — Michael P. Morris; Anthony P. Bottino

(57) ABSTRACT

The present invention encompasses compounds of the formula (I)

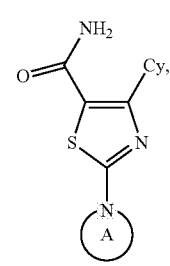

wherein the groups ring A and Cy are defined herein, which are suitable for the treatment of diseases related to BTK, process of making, pharmaceutical preparations which contain compounds and their methods of use.

16 Claims, No Drawings

HETEROAROMATIC COMPOUNDS AS BTK INHIBITORS

BACKGROUND OF THE INVENTION

1. Technical Field

The present invention relates to novel compounds which inhibit BTK and their use as medicaments.

2. Background Information

Members of the protein kinase family of human enzymes play important regulatory roles in a multitude of distinct signal transduction processes due to their post-translational modification of specific proteins via the addition of a phosphate group (Hunter, *Cell*, 1987 50, 823-829). Bruton's tyrosine kinase (BTK) is a member of the Tec family of tyrosine kinases and plays a criticial role in B cell development, activation and antibody production.

The contribution of BTK to B cell biology is exemplified in the X-linked agammaglobulinemia (XLA) immunodeficiency in humans (reviewed in Lindvall, Immunol Rev 2005, 203, 200-xxx) that display attenuated calcium signaling upon BCR engagement, lack mature B cells in periphery due to block between pro- and pre-B cells stage and have lower levels of circulating antibodies than normal healthy subjects. The outcome of recent clinical trials with B cell depleting anti-CD20 molecules in diseases such as rheumatoid arthritis (RA) and multiple sclerosis (MS) support the hypothesis that B cells offer an important intervention node for controlling autoimmune disorders (Townsend et al. 2010). As such, attenuation of B cell activation and proliferation via inhibition of BTK may offer similar therapeutic benefit and is consistent with the demonstrated resistance of BTK-deficient mice to collagen induced arthritis (Jansson, 1993, Clin Exp Immunol 94, 459-xxx) and experimental autoimmune encephalitis (Svensson et al. 2002 and Mangla et al 2004). Similarly, the clinical efficacy observed with a neutralizing antibody to the B cell stimulating factor BlyS supports a role for B cells in the pathophysiology of systemic lupus erythematosus (SLE) (La Cava 2010). Given the necessity for BTK for the production of autoantibodies, including anti-DNA antibodies, in murine models of SLE (Steinberg et al., 1982; Golding et al., 1983; Scribner et al., 1987; Seldin et al., 1987; Satterthwaite et al., 1998; Takeshita et al., 1998; Whyburn et. al., 2003), BTK inhibitors may offer therapeutic benefit to SLE patients.

Within myeloid cells, BTK signal transduction is necessary for the stimulated release of inflammatory cytokines such as TNF from stimulated monocytes (Horwood, J Exp Med, 2003, 1603-xxx) and for optimal actin cytoskeletal organization and lacunar bone resorption in isolated osteoclasts (Danks, 2011, J Bone and Mineral Research, 26, 182-192). Bone marrow derived mast cells lacking BTK exhibit impaired activation-induced degranulation and cytokine release (ref). Given the role of BTK in signal transduction processes across multiple cell types implicated in the pathogenesis of autoimmune and allergic disorders, inhibition of BTK activity may provide clinical benefit in diseases such as RA, MS, SLE, asthma and allergic disorders.

SUMMARY OF THE INVENTION

The invention comprises a novel class of heteroaromatic compounds and methods for making and using the same. These compounds are useful for the treatment of autoimmune and allergic disorders in that they exhibit good inhibitory effect upon BTK.

DETAILED DESCRIPTION OF THE INVENTION

In a first generic embodiment, there is provided a compound of the formula (I)

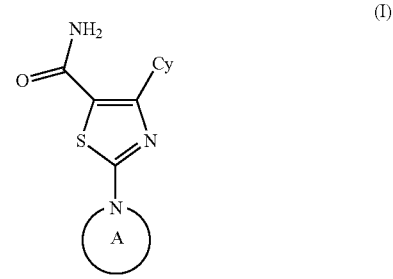

(I)

Cy is aryl, heteroaryl or heterocycle, each is substituted by $R_1$ and optionally substituted by halogen, halo $C_{1-4}$ alkyl, $C_{1-4}$ alkyl and $C_{1-4}$ alkoxy;

$R_1$ is chosen from:

L-Ar, $C_{1-6}$ alkyl, —S(O)$_m$—$R_3$ and $C_{1-6}$ alkoxy, each Ar, $C_{1-6}$ alkyl and $C_{1-6}$ alkoxy are optionally substituted by halogen, halo $C_{1-4}$ alkyl, $C_{1-4}$ alkyl, $R_2$—S(O)$_m$—, —CN, —C(O)—N($R_3$)$_2$ or $C_{1-4}$ alkoxy;

L is a linker chosen from a bond, O, >C(O), —(CH$_2$)$_n$—, —O—(CH$_2$)$_n$—, —N($R_3$)—, —N($R_3$)—(CH$_2$)$_n$—, —(CH$_2$)$_n$—N($R_3$)—, —C(O)—N($R_3$)—, —C(O)—N($R_3$)—(CH$_2$)$_n$—, —N($R_3$)—C(O)—N($R_3$)—, —N($R_3$)—C(O)—, —S(O)$_m$—N($R_3$)—, $R_3$—S(O)$_m$—, and —N($R_3$)—S(O)$_m$—, wherein the —CH$_2$— in each L can have 1-2 hydrogens replaced by $C_{1-3}$ alkyl, said $C_{1-3}$ alkyl groups can optionally cyclize to form a $C_{3-6}$ cycloalkyl ring;

Ar is carbocycle, heterocycyl or heteroaryl;

Ring A of the formula (I) is an N-linked heterocycle chosen from $C_5$-$C_{10}$ spirocycle and a nitrogen containing optionally bridged mono- or bi-cyclic heterocycle, each Ring A is substituted by one Y and optionally substituted by halogen, halo $C_{1-4}$ alkyl, $C_{1-4}$ alkyl and $C_{1-4}$ alkoxy;

Y is —(CH$_2$)$_n$—N($R_3$)—$R_4$, or Y is $R_4$, $R_4$ is

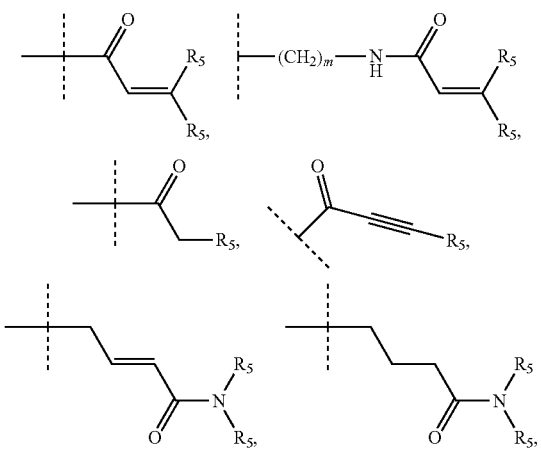

wherein R₅ cannot be hydrogen,
each n is independently 1-4;
each m is independently 0-2;

each $R_2$ and $R_3$ are independently chosen from hydrogen or $C_{1-4}$ alkyl;

each $R_5$ is independently chosen from hydrogen, halogen, $C_{1-4}$ alkyl, $C_{1-4}$ alkoxy, $C_{1-4}$ alkyl$C_{1-4}$alkoxy, $C_{1-4}$ alkylhydroxy, —(CH$_2$)$_n$-heterocycle and heterocycle each heterocycle optionally substituted by halogen, OH or $R_2$—S(O)$_m$—; each group defined above for Cy, $R_1$-$R_5$, and Y can be where possible partially or fully halogenated;

or a pharmaceutically acceptable salt thereof.

In a further embodiment, there is provided a compound of the formula (I) according to any of the embodiments herein and wherein Cy is phenyl, pyrazolyl, pyridinyl, pyrrolyl, imidazolyl, thiazolyl, furanyl, oxazolyl, isoxazolyl, thienyl, pyridazinyl, pyrimidinyl, pyrazinyl or pyranyl each is substituted by $R_1$ and optionally substituted by F, Cl or $C_{1-4}$ alkoxy;

$R_1$ is chosen from:

L-Ar and —S(O)$_m$—$R_3$, each $R_1$ is optionally substituted by Br, $C_{1-4}$ alkyl, $R_3$—S(O)$_2$—, —CN, —C(O)—NH($R_3$) and $C_{1-3}$ alkoxy;

Ar is phenyl, pyridinyl, pyridazinyl, pyrimidinyl, pyrazinyl, benzoxazolyl, indolyl, isoindolyl, benzofuranyl, benzimidazolyl, benzothiazolyl, piperidinyl, piperazinyl or pyrrolidinyl or a pharmaceutically acceptable salt thereof.

In a further embodiment, there is provided a compound of the formula (I) according to any of the embodiments herein and wherein Cy is phenyl, pyrazolyl or pyridinyl, each is substituted by $R_1$ and optionally substituted by F, Cl or $C_{1-2}$ alkoxy;

$R_1$ is L-Ar, each $R_1$ is optionally substituted by Br, $C_{1-4}$ alkyl, CH$_3$—S(O)$_2$—, —CN, —C(O)—NH($R_3$) and $C_{1-2}$ alkoxy;

Ar is phenyl, pyridinyl, pyridazinyl, pyrimidinyl, pyrazinyl, benzoxazolyl, indolyl, isoindolyl, benzofuranyl, benzimidazolyl, benzothiazolyl or piperidinyl or a pharmaceutically acceptable salt thereof.

In a further embodiment, there is provided a compound of the formula (I) according to any of the embodiments herein and wherein Cy is phenyl or pyridinyl, each is substituted by $R_1$ and optionally substituted by F, Cl or $C_{1-2}$ alkoxy;

L-Ar is optionally substituted by F, Cl, $C_{1-4}$ alkyl, CH$_3$—S(O)$_2$—, —CN, —C(O)—NH(CH$_3$) and $C_{1-2}$ alkoxy;

Ar is phenyl or pyridinyl;

or a pharmaceutically acceptable salt thereof.

In a further embodiment, there is provided a compound of the formula (I) according to any of the embodiments herein and wherein Ring A is an N-linked heterocycle chosen from:
a spirocycle chosen from each Ring A is substituted by one Y and optionally substituted by halogen or $C_{1-4}$alkyl;

or a pharmaceutically acceptable salt thereof.

In a further embodiment, there is provided a compound of the formula (I) according to any of the embodiments herein and wherein
Ring A_is chosen from:

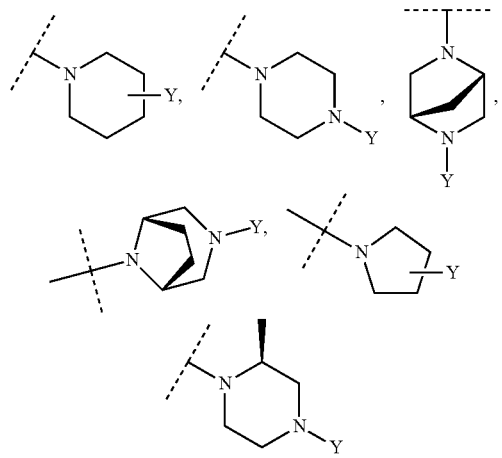

and phenyl, each Ring A is substituted by one Y and optionally substituted by halogen or $C_{1-4}$ alkyl;
or a pharmaceutically acceptable salt thereof.

In a further embodiment, there is provided a compound of the formula (I) according to any of the embodiments herein and wherein
$R_4$ is;

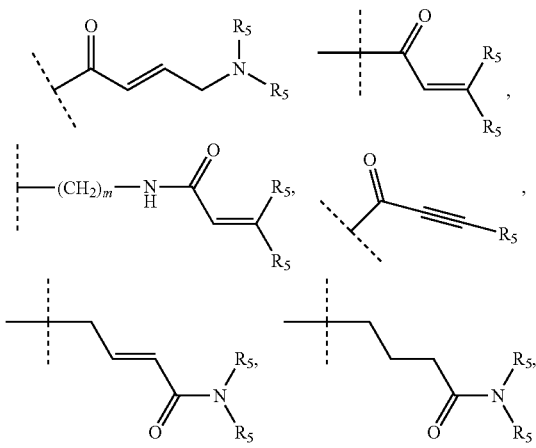

each $R_5$ is independently chosen from hydrogen, $C_{1-3}$ alkyl, halo $C_{1-3}$ alkyl, $C_{1-3}$ alkyl$C_{1-3}$ alkoxy, —$CH_2$-heterocycle and heterocycle each heterocycle optionally substituted by F, Cl, OH and $CH_3$—$S(O)_2$— and each heterocycle chosen from pyrrolidinyl, piperidinyl, morpholinyl and 1,4-oxazepane,
or a pharmaceutically acceptable salt thereof.

In a further embodiment, there is provided a compound of the formula (I) according to any of the embodiments herein and wherein
L is a linker chosen from a bond, O, —$CH_2$—, —C(O)—NH—, —NH—C(O)— and $R_3$—$S(O)_m$—;
or a pharmaceutically acceptable salt thereof.

In a further embodiment, there is provided a compound of the formula (I) according to any of the embodiments herein and wherein
L is a linker chosen from a bond, O and —$CH_2$—;
or a pharmaceutically acceptable salt thereof.

In a further embodiment, there is provided a compound of the formula (I) according to any of the embodiments herein and wherein
Cy is

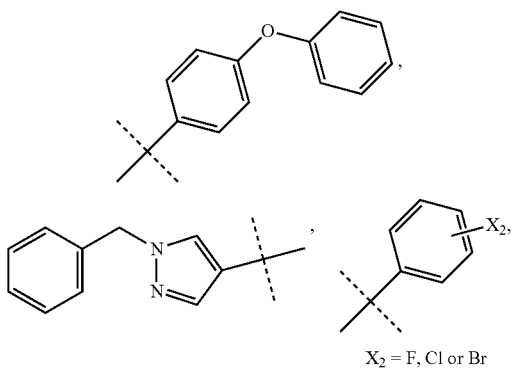

$X_2$ = F, Cl or Br

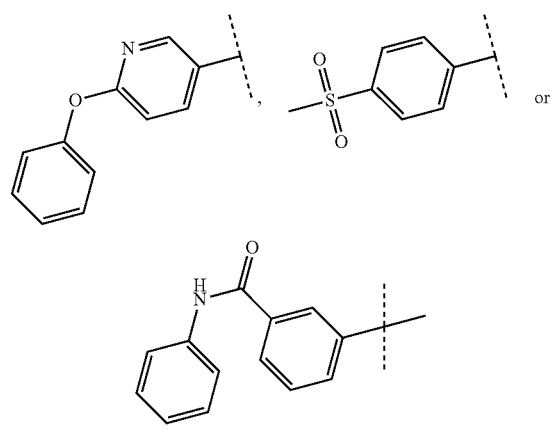

or a pharmaceutically acceptable salt thereof.

In a further embodiment, there is provided a compound of the formula (I) according to any of the embodiments herein and wherein
Cy is

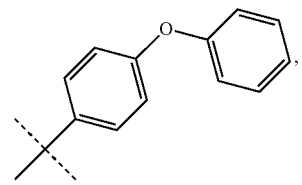

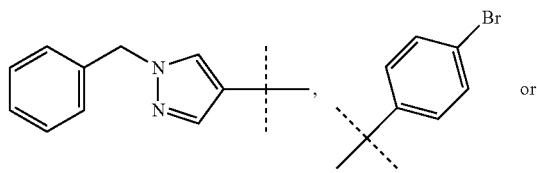

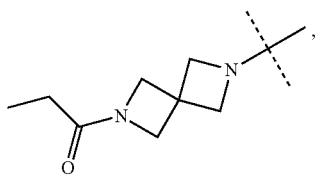
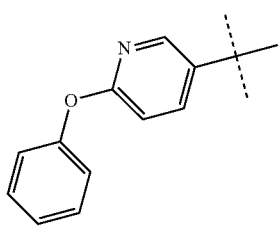
or a pharmaceutically acceptable salt thereof.
In a further embodiment, there is provided a compound of the formula (I) according to any of the embodiments herein and wherein
Y is
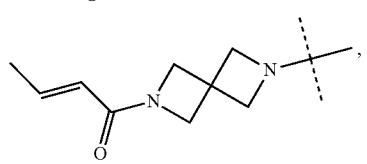
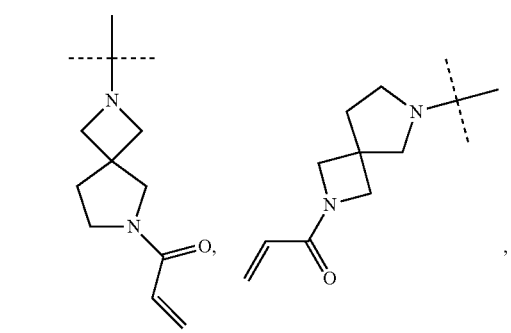
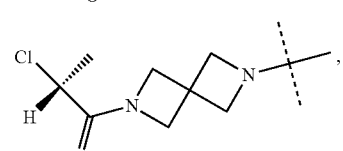
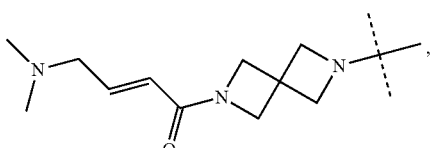
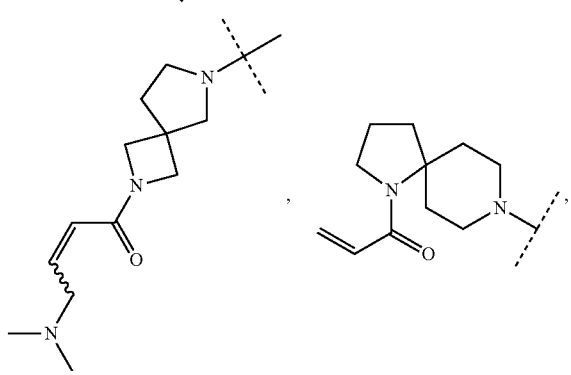
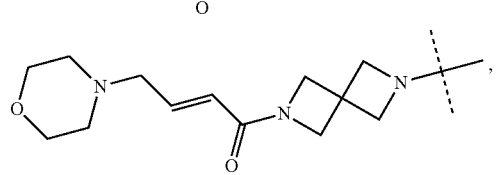
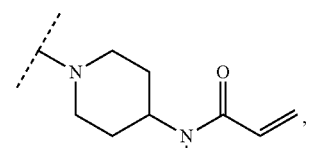
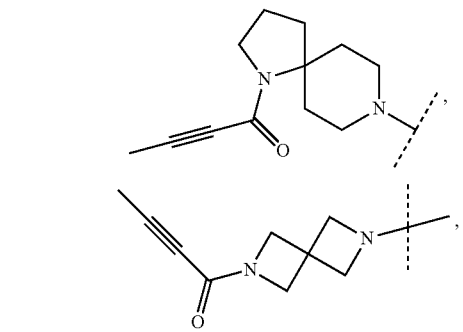
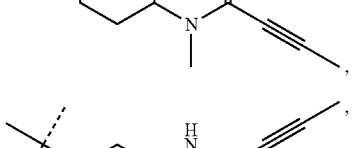
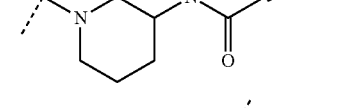
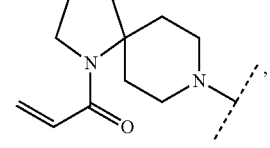
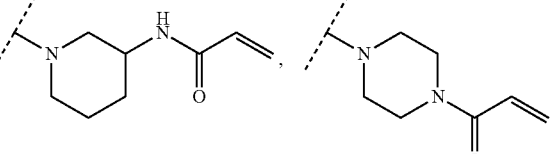
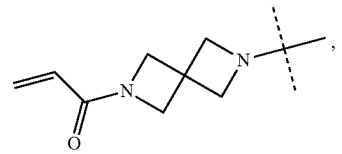
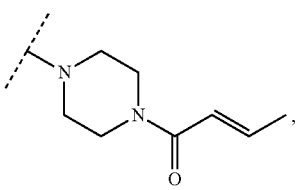

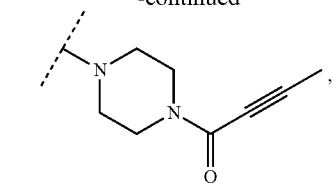
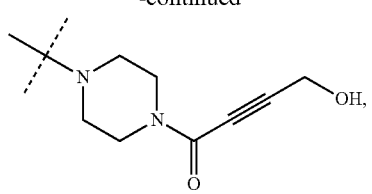
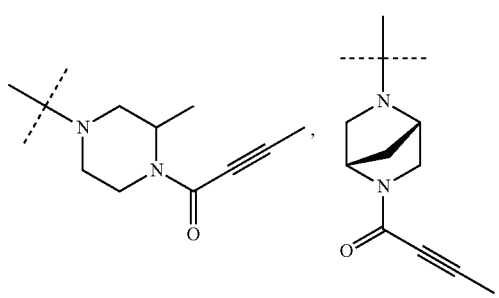
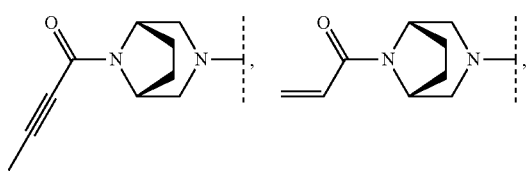
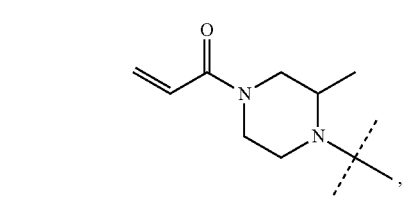
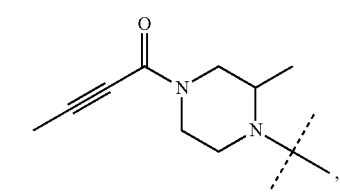
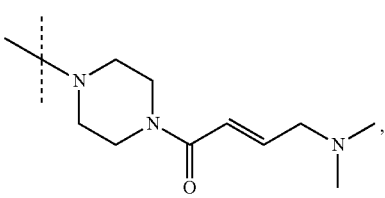
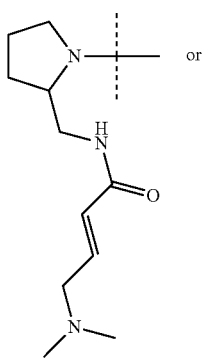
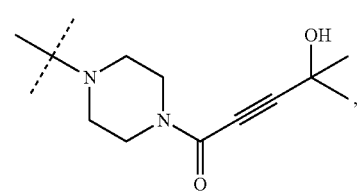
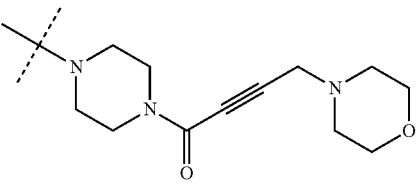
or a pharmaceutically acceptable salt thereof.
In another embodiment, the invention provides made compounds in Table I which can be made in view of the general schemes, examples and methods known in the art.

Table of compounds and Biological activity

| Example # | Compound | BTK (IC50 nM) | HPLC Method | RT (min) | m/z [M + H]+ |
|---|---|---|---|---|---|
| 1 | (structure) | 8.5 | A | 0.77 | 461.1 |
| 2 | (structure) | 4.8 | A | 2.1 | 463.2 |
| 3 | (structure) | 2.6 | A | 2.23 | 475.2 |
| 4 | (structure) | 95 | A | 2.12 | 461.2 |
| 5 | (structure) | 13 | A | 2.03 | 449.2 |
| 6 | (structure) | 0.3 | A | 1.97 | 435.2 |

-continued
| Example # | Compound | BTK (IC50 nM) | HPLC Method | RT (min) | m/z [M + H]+ |
|---|---|---|---|---|---|
| 7 | 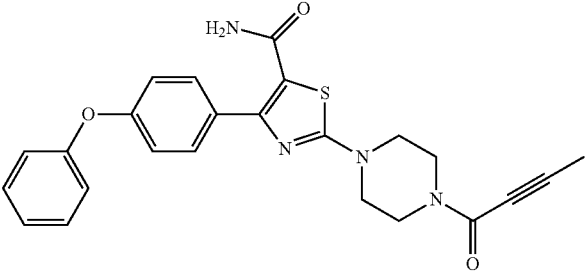 [SMILES: CC#CC(=O)N1CCN(c2nc(-c3ccc(Oc4ccccc4)cc3)c(C(N)=O)s2)CC1] | 0.67 | A | 2.12 | 447.2 |
| 8 | 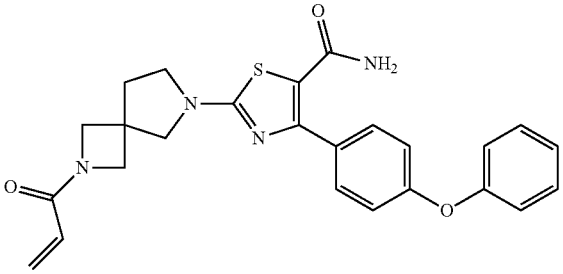 [SMILES: C=CC(=O)N1CC2(CCN(c3nc(-c4ccc(Oc5ccccc5)cc4)c(C(N)=O)s3)C2)C1] | 5.6 | A | 1.87 | 461.2 |
| 9 | 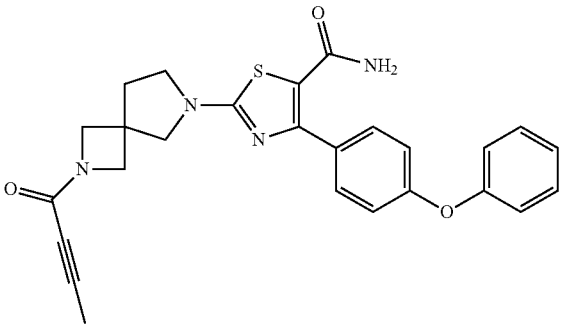 [SMILES: CC#CC(=O)N1CC2(CCN(c3nc(-c4ccc(Oc5ccccc5)cc4)c(C(N)=O)s3)C2)C1] | 4.3 | A | 2.02 | 473.2 |
| 10 | 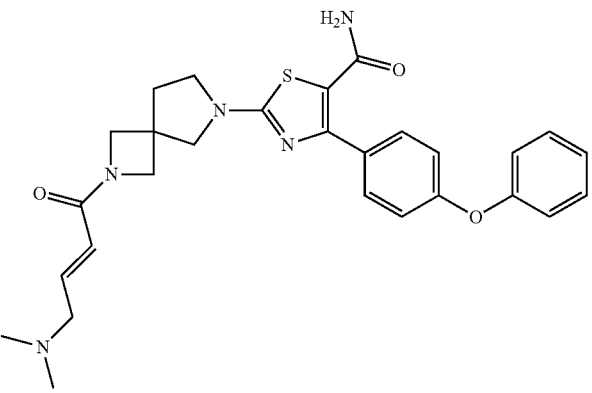 [SMILES: CN(C)C/C=C/C(=O)N1CC2(CCN(c3nc(-c4ccc(Oc5ccccc5)cc4)c(C(N)=O)s3)C2)C1] | 110 | A | 1.39 | 518.3 |

-continued

Table of compounds and Biological activity

| Example # | Compound | BTK (IC50 nM) | HPLC Method | RT (min) | m/z [M + H]+ |
|---|---|---|---|---|---|
| 11 | | 8.8 | A | 1.71 | 459.2 |
| 12 | | 4.1 | A | 1.55 | 447.2 |
| 13 | | 510 | A | 0.92 | 504.7 |
| 14 | | >1000 | A | 1.69 | 461.2 |
| 15 | | >1000 | A | 1.05 | 546.3 |

-continued

Table of compounds and Biological activity

| Example # | Compound | BTK (IC50 nM) | HPLC Method | RT (min) | m/z [M + H]+ |
|---|---|---|---|---|---|
| 16 | | 1.2 | A | 1.75 | 459.2 |
| 17 | | 0.87 | A | 1.88 | 449.2 |
| 18 | | 0.62 | A | 2.04 | 473.2 |
| 19 | | 0.48 | A | 1.88 | 461.2 |

-continued

Table of compounds and Biological activity

| Example # | Compound | BTK (IC50 nM) | HPLC Method | RT (min) | m/z [M + H]+ |
|---|---|---|---|---|---|
| 20 | | 350 | A | 0.83 | 483.2 |
| 21 | | 1.2 | A | 2.04 | 461.2 |
| 22 | | 2.0 | A | 1.28 | 492.3 |
| 23 | | 43 | A | 2.2 | 489.3 |
| 24 | | 150 | A | 2.24 | 501.3 |

-continued

| Table of compounds and Biological activity | | | | | |
|---|---|---|---|---|---|
| Example # | Compound | BTK (IC50 nM) | HPLC Method | RT (min) | m/z [M + H]+ |
| 25 | | 1.0 | A | 2.03 | 461.2 |
| 26 | | 69 | A | 1.21 | 480.3 |
| 27 | | 710 | A | 1.22 | 423.2 |
| 28 | | >1000 | A | 1.38 | 435.2 |
| 29 | | 6.6 | A | 1.46 | 420.8 |

| Example # | Compound | BTK (IC50 nM) | HPLC Method | RT (min) | m/z [M + H]+ |
|---|---|---|---|---|---|
| 30 | (structure: 4-bromophenyl thiazole carboxamide with piperazine-butynoyl) | 73 | A | 1.64 | 434.9 |
| 31 | (structure: phenoxyphenyl thiazole carboxamide with diazaspiro propanoyl) | >1000 | A | 1.67 | 449.1 |
| 32 | (structure: phenoxypyridyl thiazole carboxamide with piperazine-acryloyl) | 17 | A | 1.43 | 436.1 |
| 33 | (structure: phenoxypyridyl thiazole carboxamide with piperazine-butynoyl) | 180 | A | 1.6 | 448.1 |
| 34 | (structure: phenoxypyridyl thiazole carboxamide with piperazine-crotonoyl) | 700 | A | 1.61 | 450.1 |

-continued
| Table of compounds and Biological activity | | | | | |
|---|---|---|---|---|---|
| Example # | Compound | BTK (IC50 nM) | HPLC Method | RT (min) | m/z [M + H]+ |
| 35 | 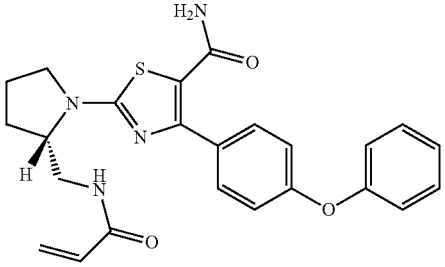 [SMILES: C=CC(=O)NC[C@@H]1CCCN1c1nc(-c2ccc(Oc3ccccc3)cc2)c(C(N)=O)s1] | 11 | A | 1.99 | 449.3 |
| 36 | 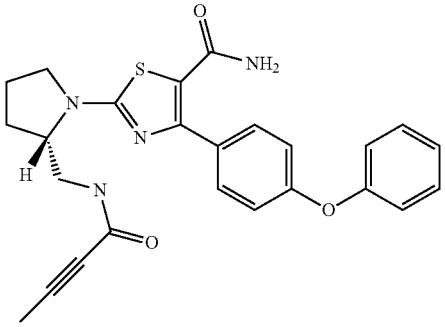 [SMILES: CC#CC(=O)NC[C@@H]1CCCN1c1nc(-c2ccc(Oc3ccccc3)cc2)c(C(N)=O)s1] | 14 | A | 2.1 | 462.6 |
| 37 | 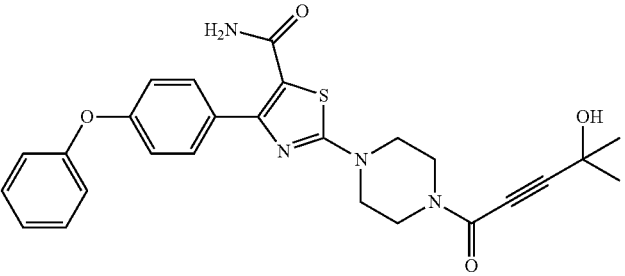 [SMILES: CC(C)(O)C#CC(=O)N1CCN(c2nc(-c3ccc(Oc4ccccc4)cc3)c(C(N)=O)s2)CC1] | 0.65 | A | 2.04 | 491.6 |
| 38 | 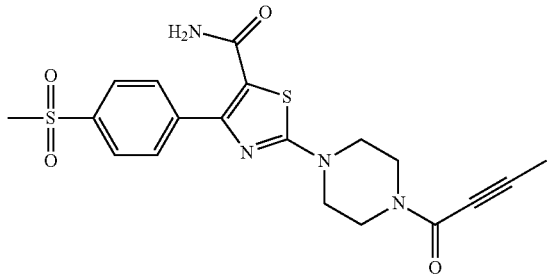 [SMILES: CC#CC(=O)N1CCN(c2nc(-c3ccc(S(C)(=O)=O)cc3)c(C(N)=O)s2)CC1] | >1000 | A | 0.66 | 433.3 |
| 39 | 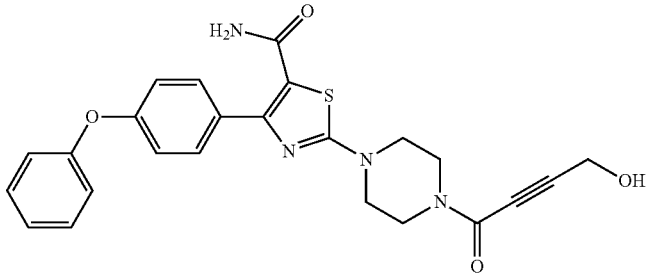 [SMILES: NC(=O)c1sc(N2CCN(C(=O)C#CCO)CC2)nc1-c1ccc(Oc2ccccc2)cc1] | 0.69 | A | 1.8 | 463.5 |

-continued

Table of compounds and Biological activity

| Example # | Compound | BTK (IC50 nM) | HPLC Method | RT (min) | m/z [M + H]+ |
|---|---|---|---|---|---|
| 40 | | 120 | A | 2.03 | 450.7 |
| 41 | | 30 | A | 2.15 | 462.7 |
| 42 | | 0.7 | A | 1.53 | 533.7 |
| 43 | | 52 | A | 1.34 | 506.6 |

Table of compounds and Biological activity

| Example # | Compound | BTK (IC50 nM) | HPLC Method | RT (min) | m/z [M + H]+ |
|---|---|---|---|---|---|
| 44 | 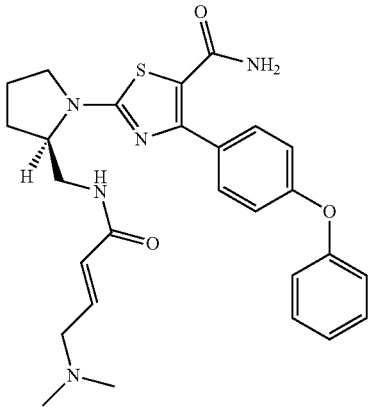 [SMILES: CN(C)C/C=C/C(=O)NC[C@H]1CCCN1c1nc(-c2ccc(Oc3ccccc3)cc2)c(C(N)=O)s1] | 560 | A | 1.36 | 506.2 |
| 45 | 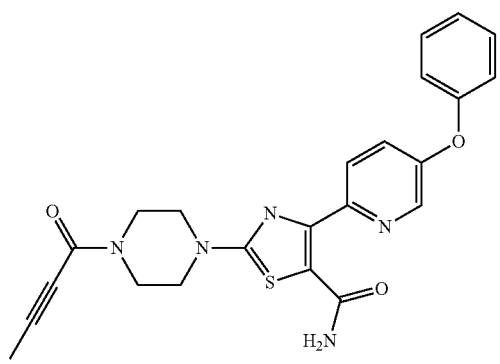 | 40 | A | 0.94 | 448.1 |
| 46 | 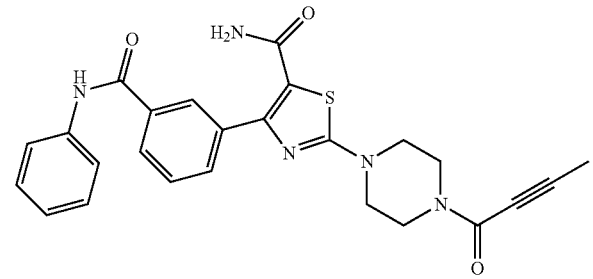 [SMILES: CC#CC(=O)N1CCN(c2nc(-c3cccc(C(=O)Nc4ccccc4)c3)c(C(N)=O)s2)CC1] | >1000 | A | 0.83 | 474.2 | or the pharmaceutically acceptable salts thereof.

The present invention further relates to metabolites, and prodrugs of compounds of the formula (I).

The present invention further relates to a pharmaceutically acceptable salt of a compound of the formula (I) with anorganic or organic acids or bases.

In another aspect the invention relates to compounds of formula (I)—or the pharmaceutically acceptable salts thereof—as medicaments.

In another aspect the invention relates to compounds of formula (I)—or the pharmaceutically acceptable salts thereof—for use in a method for treatment of a patient.

In another aspect the invention relates to compounds of formula (I)—or the pharmaceutically acceptable salts thereof—for use in the treatment of autoimmune diseases and allergic disorders.

In another aspect the invention relates to the use of compounds of formula (I)—or the pharmaceutically acceptable salts thereof—for preparing a pharmaceutical composition for the treatment of autoimmune diseases and allergic disorders.

In another aspect the invention relates to a method for the treatment of autoimmune diseases and allergic disorders comprising administering a therapeutically effective amount of a compound of formula (I)—or one of the pharmaceutically acceptable salts thereof—to a patient.

In another aspect the invention relates to a pharmaceutical preparation containing as active substance one or more compounds of formula (I)—or the pharmaceutically acceptable salts thereof—optionally in combination with conventional excipients and/or carriers.

DEFINITIONS

Terms that are not specifically defined here have the meanings that are apparent to the skilled man in the light of the overall disclosure and the context as a whole.

As used herein, the following definitions apply, unless stated otherwise:

The use of the prefix $C_{x-y}$, wherein x and y each represent a natural number, indicates that the chain or ring structure or combination of chain and ring structure as a whole, specified and mentioned in direct association, may consist of a maximum of y and a minimum of x carbon atoms.

Alkyl denotes monovalent, saturated hydrocarbon chains, which may be present in both straight-chain (unbranched) and branched form. If an alkyl is substituted, the substitution may take place independently of one another, by mono- or polysubstitution in each case, on all the hydrogen-carrying carbon atoms.

For example, the term "$C_{1-5}$alkyl" includes for example $H_3C$—, $H_3C$—$CH_2$—, $H_3C$—$CH_2$—$CH_2$—, $H_3C$—$CH(CH_3)$—, $H_3C$—$CH_2$—$CH_2$—$CH_2$—, $H_3C$—$CH_2$—$CH(CH_3)$—, $H_3C$—$CH(CH_3)$—$CH_2$—, $H_3C$—$C(CH_3)_2$—, $H_3C$—$CH_2$—$CH_2$—$CH_2$—$CH_2$—, $H_3C$—$CH_2$—$CH_2$—$CH(CH_3)$—, $H_3C$—$CH_2$—$CH(CH_3)$—$CH_2$—, $H_3C$—$CH(CH_3)$—$CH_2$—$CH_2$—, $H_3C$—$CH_2$—$C(CH_3)_2$—, $H_3C$—$C(CH_3)_2$—$CH_2$—, $H_3C$—$CH(CH_3)$—$CH(CH_3)$— and $H_3C$—$CH_2$—$CH(CH_2CH_3)$—.

Further examples of alkyl are methyl (Me; —$CH_3$), ethyl (Et; —$CH_2CH_3$), 1-propyl (n-propyl; n-Pr; —$CH_2CH_2CH_3$), 2-propyl (i-Pr; iso-propyl; —$CH(CH_3)_2$), 1-butyl (n-butyl; n-Bu; —$CH_2CH_2CH_2CH_3$), 2-methyl-1-propyl (iso-butyl; i-Bu; —$CH_2CH(CH_3)_2$), 2-butyl (sec-butyl; sec-Bu; —$CH(CH_3)CH_2CH_3$), 2-methyl-2-propyl (tert-butyl; t-Bu; —$C(CH_3)_3$), 1-pentyl (n-pentyl; —$CH_2CH_2CH_2CH_2CH_3$), 2-pentyl (—$CH(CH_3)CH_2CH_2CH_3$), 3-pentyl (—$CH(CH_2CH_3)_2$), 3-methyl-1-butyl (iso-pentyl; —$CH_2CH_2CH(CH_3)_2$), 2-methyl-2-butyl (—$C(CH_3)_2CH_2CH_3$), 3-methyl-2-butyl (—$CH(CH_3)CH(CH_3)_2$), 2,2-dimethyl-1-propyl (neo-pentyl; —$CH_2C(CH_3)_3$), 2-methyl-1-butyl (—$CH_2CH(CH_3)CH_2CH_3$), 1-hexyl (n-hexyl; —$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)C(CH_3)_3$), 2,3-dimethyl-1-butyl (—$CH_2CH(CH_3)CH(CH_3)CH_3$), 2,2-dimethyl-1-butyl (—$CH_2C(CH_3)_2CH_2CH_3$), 3,3-dimethyl-1-butyl (—$CH_2CH_2C(CH_3)_3$), 2-methyl-1-pentyl (—$CH_2CH(CH_3)CH_2CH_2CH_3$), 3-methyl-1-pentyl (—$CH_2CH_2CH(CH_3)CH_2CH_3$), 1-heptyl (n-heptyl), 2-methyl-1-hexyl, 3-methyl-1-hexyl, 2,2-dimethyl-1-pentyl, 2,3-dimethyl-1-pentyl, 2,4-dimethyl-1-pentyl, 3,3-dimethyl-1-pentyl, 2,2,3-trimethyl-1-butyl, 3-ethyl-1-pentyl, 1-octyl (n-octyl), 1-nonyl (n-nonyl); 1-decyl (n-decyl) etc.

By the terms propyl, butyl, pentyl, hexyl, heptyl, octyl, nonyl, decyl etc. without any further definition are meant saturated hydrocarbon groups with the corresponding number of carbon atoms, wherein all isomeric forms are included.

The above definition for alkyl also applies if alkyl is a part of another (combined) group such as for example $C_{x-y}$alkylamino or $C_{x-y}$alkoxy.

Unlike alkyl, alkenyl consists of at least two carbon atoms, wherein at least two adjacent carbon atoms are joined together by a C—C double bond and a carbon atom can only be part of one C—C double bond. If in an alkyl as hereinbefore defined having at least two carbon atoms, two hydrogen atoms on adjacent carbon atoms are formally removed and the free valencies are saturated to form a second bond, the corresponding alkenyl is formed.

Alkenyl may optionally be present in the cis or trans or E or Z orientation with regard to the double bond(s).

Unlike alkyl, alkynyl consists of at least two carbon atoms, wherein at least two adjacent carbon atoms are joined together by a C—C triple bond. If in an alkyl as hereinbefore defined having at least two carbon atoms, two hydrogen atoms in each case at adjacent carbon atoms are formally removed and the free valencies are saturated to form two further bonds, the corresponding alkynyl is formed.

Haloalkyl (haloalkenyl, haloalkynyl) is derived from the previously defined alkyl (alkenyl, alkynyl) by replacing one or more hydrogen atoms of the hydrocarbon chain independently of one another by halogen atoms, which may be identical or different. If a haloalkyl (haloalkenyl, haloalkynyl) is to be further substituted, the substitutions may take place independently of one another, in the form of mono- or polysubstitutions in each case, on all the hydrogen-carrying carbon atoms.

Examples of haloalkyl (haloalkenyl, haloalkynyl) are —$CF_3$, —$CHF_2$, —$CH_2F$, —$CF_2CF_3$, —$CHFCF_3$, —$CH_2CF_3$, —$CF_2CH_3$, —$CHFCH_3$, —$CF_2CF_2CF_3$, —$CF_2CH_2CH_3$, —$CF=CF_2$, —$CCl=CH_2$, —$CBr=CH_2$, —$C\equiv C-CF_3$, —$CHFCH_2CH_3$, —$CHFCH_2CF_3$ etc.

Halogen relates to fluorine, chlorine, bromine and/or iodine atoms.

Cycloalkyl is made up of the subgroups monocyclic hydrocarbon rings, bicyclic hydrocarbon rings and spiro-hydrocarbon rings. The systems are saturated. In bicyclic hydrocarbon rings two rings are joined together so that they have at least two carbon atoms together.

If a cycloalkyl is to be substituted, the substitutions may take place independently of one another, in the form of mono- or polysubstitutions in each case, on all the hydrogen-carrying carbon atoms. Cycloalkyl itself may be linked as a substituent to the molecule via every suitable position of the ring system.

Examples of cycloalkyl are cyclopropyl, cyclobutyl, cyclopentyl, cyclohexyl, cycloheptyl. Corresponding groups are an example:

cyclohexyl

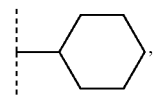

wherein the dashed line indicates the point of attachment.

Spirocycle is a spiro-hydrocarbon ring one carbon atom (spiroatom) belongs to two rings together.

Aryl denotes mono-, bi- or tricyclic carbocycles with at least one aromatic carbocycle. Preferably, it denotes a monocyclic group with six carbon atoms (phenyl) or a bicyclic group with nine or ten carbon atoms (two six-membered rings or one six-membered ring with a five-membered ring), wherein the second ring may also be aromatic or, however, may also be saturated or partially saturated.

If an aryl is to be substituted, the substitutions may take place independently of one another, in the form of mono- or polysubstitutions in each case, on all the hydrogen-carrying carbon atoms. Aryl itself may be linked as a substituent to the molecule via every suitable position of the ring system.

Examples of aryl are phenyl and naphthyl.

The above definition of aryl also applies if aryl is part of another (combined) group as for example in arylamino, aryloxy or arylalkyl.

Heterocyclyl denotes ring systems, which are derived from the previously defined cycloalkyl or spirocycle by replacing one or more of the groups —CH$_2$— independently of one another in the hydrocarbon rings by the groups —O—, —S— or —NH—, wherein a total of not more than five heteroatoms may be present, at least one carbon atom may be present between two oxygen atoms and between two sulphur atoms or between one oxygen and one sulphur atom and the ring as a whole must have chemical stability. Heteroatoms may optionally be present in all the possible oxidation stages (sulphur sulphoxide —SO—, sulphone —SO$_2$—; nitrogen N-oxide).

If a heterocyclyl is substituted, the substitutions may take place independently of one another, in the form of mono- or polysubstitutions in each case, on all the hydrogen-carrying carbon and/or nitrogen atoms. Heterocyclyl itself may be linked as a substituent to the molecule via every suitable position of the ring system.

Examples of heterocyclyl are piperidinyl, piperazinyl, pyrrolidinyl, morpholinyl, or the following heterocyclic spirocycles

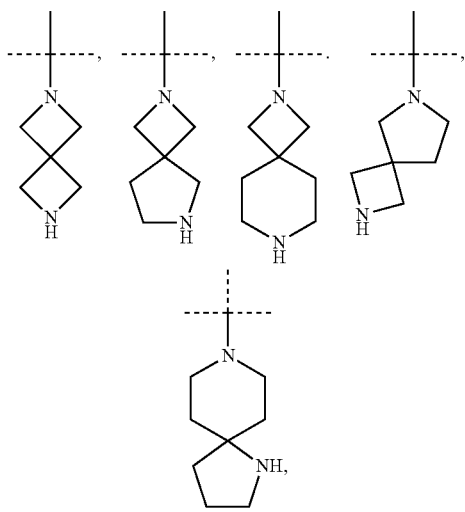

or the following bridged heterocycles

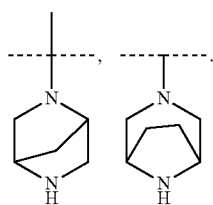

Heteroaryl denotes monocyclic heteroaromatic rings or polycyclic rings with at least one heteroaromatic ring, which compared with the corresponding aryl or cycloalkyl, instead of one or more carbon atoms, one or more identical or different heteroatoms, selected independently of one another from among nitrogen, sulphur and oxygen, wherein the resulting group must be chemically stable. The prerequisite for the presence of heteroaryl is a heteroatom and a heteroaromatic system.

If a heteroaryl is to be substituted, the substitutions may take place independently of one another, in the form of mono- or polysubstitutions in each case, on all the hydrogen-carrying carbon and/or nitrogen atoms. Heteroaryl itself may be linked as a substituent to the molecule via every suitable position of the ring system, both carbon and nitrogen.

Examples of heteroaryl are pyridinyl, pyridazinyl, pyrimidinyl, pyrazinyl, benzoxazolyl, indolyl, isoindolyl, benzofuranyl, benzimidazolyl, benzothiazolyl, pyrrolyl, imidazolyl, thiazolyl, furanyl, oxazolyl, isoxazolyl, thienyl, pyranyl, and the like.

Heteroatoms may optionally be present in all the possible oxidation stages (sulphur sulphoxide —SO—, sulphone —SO$_2$—; nitrogen N-oxide).

Carbocycles include hydrocarbon rings containing from three to twelve carbon atoms. These carbocycles may be either aromatic either aromatic or non-aromatic ring systems. The non-aromatic ring systems may be mono- or polyunsaturated. Preferred carbocycles include but are not limited to cyclopropyl, cyclobutyl, cyclopentyl, cyclopentenyl, cyclohexyl, cyclohexenyl, cycloheptanyl, cycloheptenyl, phenyl, indanyl, indenyl, benzocyclobutanyl, dihydronaphthyl, tetrahydronaphthyl, naphthyl, decahydronaphthyl, benzocycloheptanyl and benzocycloheptenyl.

All cyclic and acyclic systems defined in this section hereinabove shall be understood to be optionally partially or fully halogenated where possible and unless otherwise indicated.

Stereochemistry/Solvates/Hydrates:

Unless specifically indicated, throughout the specification and appended claims, a given chemical formula or name shall encompass tautomers and all stereo, optical and geometrical isomers (e.g. enantiomers, diastereomers, E/Z isomers, etc.) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof. The compounds and salts of the invention can exist in unsolvated as well as solvated forms with pharmaceutically acceptable solvents such as water, ethanol and the like. In general, the solvated forms such as hydrates are considered equivalent to the unsolvated forms for the purposes of the invention.

Salts:

The phrase "pharmaceutically acceptable" is employed herein to refer to those compounds, materials, compositions, and/or dosage forms which are, within the scope of sound medical judgement, suitable for use in contact with the tissues of human beings and animals without excessive toxicity, irritation, allergic response, or other problem or complication, and commensurate with a reasonable benefit/risk ratio.

As used herein "pharmaceutically acceptable salts" refers to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like.

For example, such salts include acetates, ascorbates, benzenesulphonates, benzoates, besylates, bicarbonates, bitartrates, bromides/hydrobromides, Ca-edetates/edetates, camsylates, carbonates, chlorides/hydrochlorides, citrates, edisylates, ethane disulphonates, estolates esylates, fumarates, gluceptates, gluconates, glutamates, glycolates, glycollylarsnilates, hexylresorcinates, hydrabamines, hydroxymaleates, hydroxynaphthoates, iodides, isothionates, lactates, lactobionates, malates, maleates, mandelates, methanesulphonates, mesylates, methylbromides, methylnitrates, methylsulphates, mucates, napsylates, nitrates, oxalates, pamoates, pantothenates, phenyl acetates, phosphates/ diphosphates, polygalacturonates, propionates, salicylates, stearates, subacetates, succinates, sulphamides, sulphates, tannates, tartrates, teoclates, toluenesulphonates, triethiodides, ammonium, benzathines, chloroprocaines, cholines, diethanolamines, ethylenediamines, meglumines and procaines.

Further pharmaceutically acceptable salts can be formed with cations from metals like aluminium, calcium, lithium, magnesium, potassium, sodium, zinc and the like (also see Pharmaceutical salts, Birge, S. M. et al., J. Pharm. Sci., (1977), 66, 1-19).

The pharmaceutically acceptable salts of the present invention can be synthesised from the parent compound which contains a basic or acidic moiety by conventional chemical methods. Generally, such salts can be prepared by reacting the free acid or base form of these compounds with a sufficient amount of the appropriate base or acid in water or in an organic diluent like ether, ethyl acetate, ethanol, isopropanol, or acetonitrile, or a mixture thereof.

Salts of other acids than those mentioned above which for example are useful for purifying or isolating the compounds of the present invention (e.g. trifluoroacetates), also comprise a part of the invention.

Some abbreviated notations and their structure correspondences are listed below:

In a representation such as for example

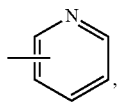

the solid line means that the ring system may be attached to the molecule via the carbon atom 1, 2 or 3, and is thus equivalent to the following representation

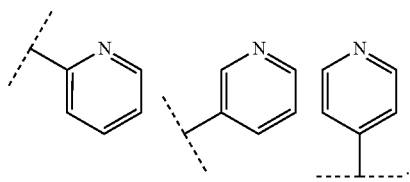

By a therapeutically effective amount for the purposes of this invention is meant a quantity of substance that is capable of obviating symptoms of illness or alleviating these symptoms, or which prolong the survival of a treated patient.

| List of abbreviations | |
|---|---|
| Ac | Acetyl |
| ACN | Acetonitrile |
| aq | Aqueous |
| ATP | adenosine triphosphate |
| Bn | Benzyl |
| Bu | Butyl |
| Boc | tert-butyloxycarbonyl |
| cat | Catalyst |
| conc | concentrated |
| d | day(s) |
| TLC | thin layer chromatography |
| DIEA | N,N-diisopropylethylamine |
| DMAP | 4-N,N-dimethylaminopyridine |
| DME | 1,2-dimethoxyethane |
| DMF | N,N-dimethylformamide |

-continued

| List of abbreviations | |
|---|---|
| DMSO | Dimethylsulphoxide |
| dppf | 1.1'-bis(diphenylphosphino)ferrocene |
| EDC | 1-Ethyl-3-(3-dimethylaminopropyl)carbodiimide |
| ESI | electron spray ionization |
| Et | Ethyl |
| Et$_2$O | diethyl ether |
| EtOAc | ethyl acetate |
| EtOH | Ethanol |
| h | hour(s) |
| HATU | O-(7-azabenzotriazol-1-yl)-N,N,N',N'-tetramethyl-uronium hexafluorophosphate |
| Hep | Heptane |
| HPLC | high performance liquid chromatography |
| i | Iso |
| LC | liquid chromatography |
| LiHMDS | lithium bis(trimethylsilyl)amide |
| sln. | Solution |
| mCPBA | 3-Chloroperoxbenzoic acid |
| Me | Methyl |
| MeOH | Methanol |
| min | Minutes |
| MPLC | medium pressure liquid chromatography |
| MS | mass spectrometry |
| NBS | N-bromo-succinimide |
| NIS | N-iodo-succinimide |
| NMM | N-methylmorpholine |
| NMP | N-methylpyrrolidone |
| NP | normal phase |
| n.a. | not available |
| PBS | phosphate-buffered saline |
| Ph | Phenyl |
| Pr | Propyl |
| Pyr | Pyridine |
| rac | Racemic |
| Rf (R$_f$) | retention factor |
| RP | reversed phase |
| RT | Retention time (HPLC) |
| rt | ambient temperature |
| TBAF | tetrabutylammonium fluoride |
| TBDMS | tert-butyldimethylsilyl |
| TBME | tert-butylmethylether |
| TBTU | O-(benzotriazol-1-yl)-N,N,N',N'-tetramethyl-uronium tetrafluoroborate |
| tBu | tert-butyl |
| TEA | Triethylamine |
| temp. | Temperature |
| tert | Tertiary |
| Tf | Triflate |
| TFA | trifluoroacetic acid |
| THF | Tetrahydrofuran |
| TMS | Trimethylsilyl |
| TRIS | tris(hydroxymethyl)-aminomethane |
| Ts | p-Tosyl |
| TsOH | p-toluenesulphonic acid |
| UV | Ultraviolet |

Features and advantages of the present invention will become apparent from the following detailed examples which illustrate the fundamentals of the invention by way of example without restricting its scope:

Preparation of the Compounds According to the Invention

General Synthetic Methods

Compounds of formula I may be prepared as shown in General Scheme Ia and Ib below.

Scheme Ia:

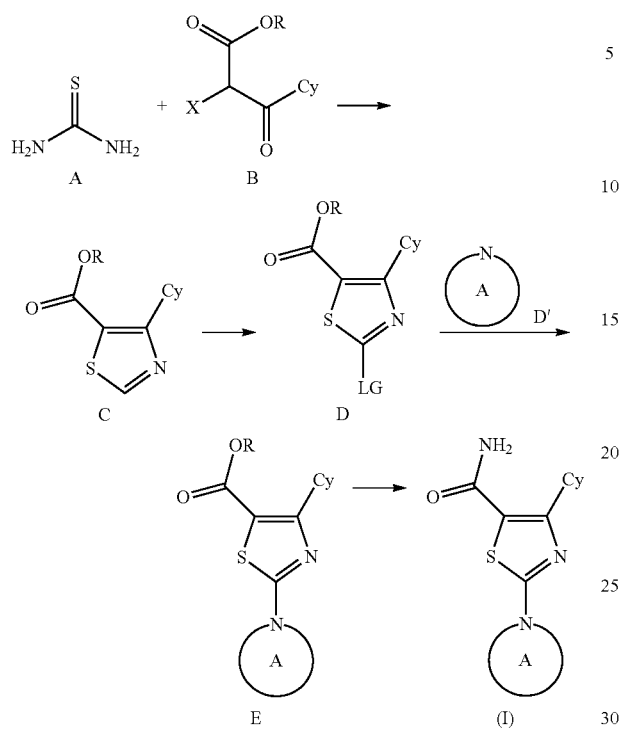

In scheme Ia, A is condensed with B to afford C, C reacted with cupric compound containing a leaving group (LG) to afford D, D' is treated with suitable base and reacted with D to afford E, E is treated with suitable base such as DIPEA or TEA and suitable coupling reagent such as EDCI, TBTU, PyBOP or HATU to afford the compound of general formula (I).

Scheme Ib:

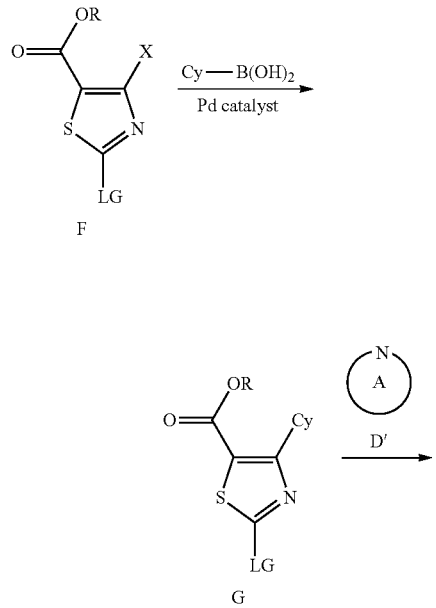

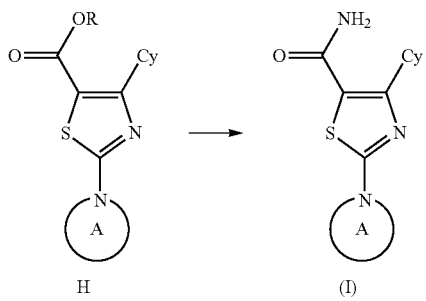

In Scheme Ib, G can be prepared from compound F using an appropriate boronic acid or pinacol ester, in the presence of a suitable palladium catalyst system, for example bis(diphenylphosphino)ferrocene palladium (II) chloride complex or tetrakis(triphenylphosphine)palladium (0) in the presence of an inoranic base like potassium carbonate, cesium carbonate or potassium phosphate in a suitable solvent system like combinations of dioxane and water. D' is treated with suitable base and reacted with G to afford H, H is treated with suitable base such as DIPEA or TEA and suitable coupling reagent such as EDCI, TBTU, PyBOP or HATU to afford the compound of general formula (I).

Method 1

Synthesis of Intermediate 1-4

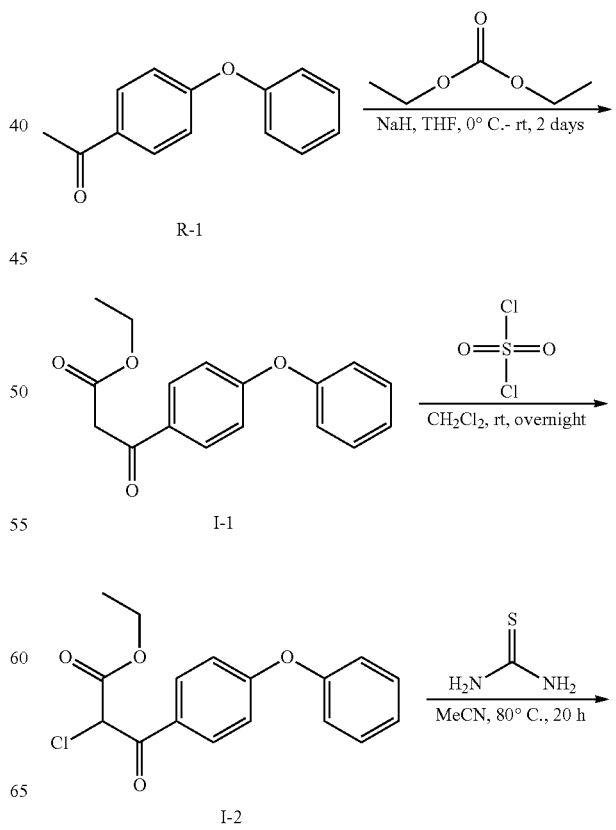

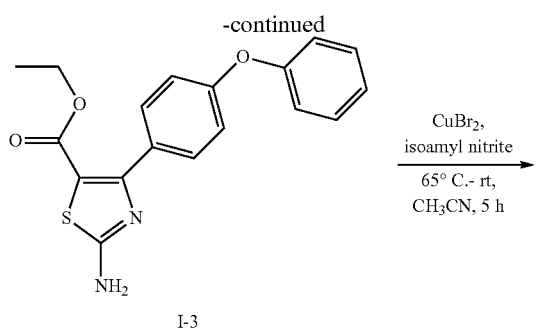

I-3

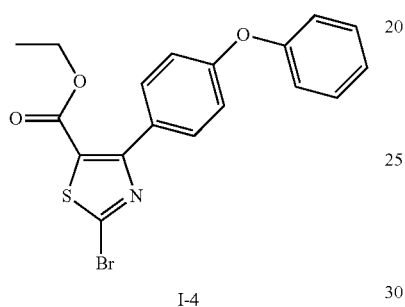

I-4

To a suspension of 60% NaH (28.3 g, 0.71 mol) in THF (500 mL), a solution of R-1 (100.0 g, 0.47 mol) in THF (600 mL) is added. After addition is complete, the reaction mixture is stirred for 10 min and then treated with carbonic acid diethyl ester (111.0 g, 0.94 mol). The mixture is stirred at room temperature for 2 days then treated with saturated aqueous $NH_4Cl$ (100 mL). The mixture is extracted with EtOAc, washed with brine, dried over sodium sulfate and concentrated in vacuo. The residue is purified via column chromatography on silica gel to afford I-1 (69.0 g, 52%).

A stirred solution of 1-1 (69.0 g, 0.24 mol) in $CH_2Cl_2$ (600.0 mL) is treated with dichlorosulfone (48.0 g, 0.36 mol) and then stirred at room temperature overnight. The volatiles are removed in vacuo. The residue is extracted with EtOAc, dried over $MgSO_4$, filtered and concentrated in vacuo to afford 1-2 (48.0 g, 62%).

The mixture of 1-2 (48.0 g, 0.15 mol) and thiourea (11.4 g, 0.15 mol) in MeCN (600.0 mL) is heated to 80° C. for 20 hours. The mixture is concentrated in vacuo then pardoned between water and DCM. The organics are collected, dried over $MgSO_4$, filtered and concentrated in vacuo. The residue is purified via column chromatography on silica gel to afford 1-3 (29.0 g, 58%).

1-3 (29.9 g, 0.085 mol) is dissolved in MeCN (200.0 mL) and treated with cupric bromide (11.3 g, 0.051 mol). The mixture is heated to 65° C. and treated with a solution of isoamyl nitrite (15.4 g, 0.13 mol) in MeCN (100.0 mL) slowly. Upon completion of the addition, the mixture is cooled to room temperature and stirred for 5 hours. The solvent is removed and the residue is diluted with 2M aqueous HCl and extracted with DCM. The organics are collected, dried over $MgSO_4$, filtered and concentrated in vauco. The residue is purified via column chromatography to afford 1-4 (23.0 g, 68%) m/z 406.0[M+H].

The following intermediate was prepared in similar fashion:

| structure | Intermediate | m/z |
|---|---|---|
| 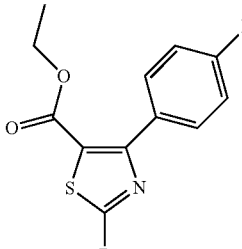 | I-5 | 391.8 |

Method 2

Synthesis of Intermediate 1-6

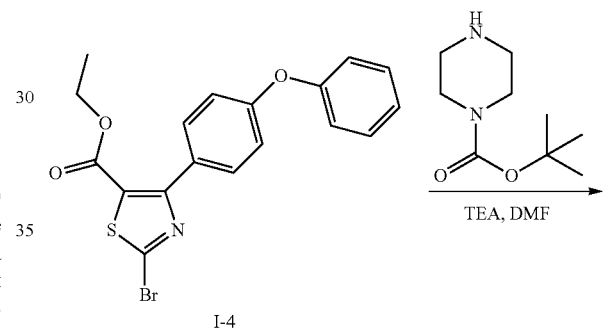

To a stirred solution of 1-4 (0.4 g, 1.0 mmol) in DMF piperazine-1-carboxylic acid tert-butyl ester (0.27 g, 1.5 mmol) and TEA (0.4 mL, 3.0 mmol) is added. The reaction solution is heated to 60° C. After 12 hours, the reaction solution is concentrated in vacuo and the residue is purified via Combi-flash chromatography on silica gel (using a solvent gradient from 0-23% ethyl acetate in heptanes) to afford 1-6 (0.48 g, 95.2%), m/z 510.22 [M+H], RT 1.32 min.

The following intermediates were prepared in a similar manner:

| Structure | Intermediate | m/z |
|---|---|---|
| 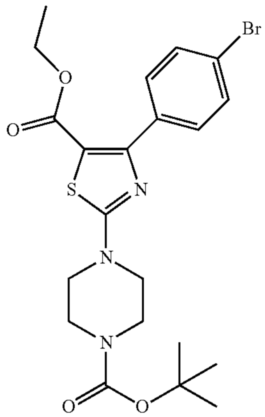 [SMILES: CCOC(=O)c1sc(N2CCN(C(=O)OC(C)(C)C)CC2)nc1-c1ccc(Br)cc1] | I-7 | 496.16 |
| 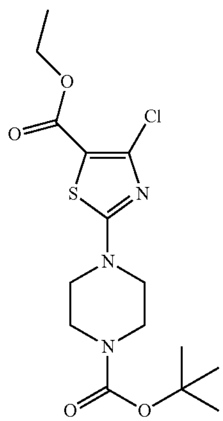 [SMILES: CCOC(=O)c1sc(N2CCN(C(=O)OC(C)(C)C)CC2)nc1Cl] | I-8 | 362.13 |
| 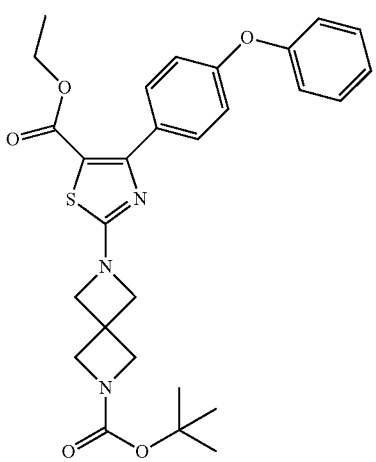 [SMILES: CCOC(=O)c1sc(N2CC3(CN(C(=O)OC(C)(C)C)C3)C2)nc1-c1ccc(Oc2ccccc2)cc1] | I-9 | 522.28 |
| | I-10 | 538.28 |
| | I-11 | 524.32 |
| | I-12 | 536.27 |

43 -continued

| Structure | Intermediate | m/z |
|---|---|---|
| 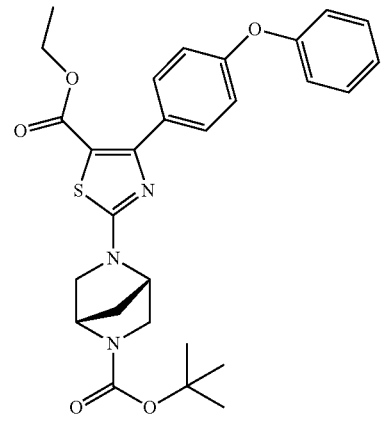 [SMILES: CCOC(=O)c1sc(N2C[C@@H]3C[C@H]2CN3C(=O)OC(C)(C)C)nc1-c1ccc(Oc2ccccc2)cc1] | I-13 | 522.30 |
| 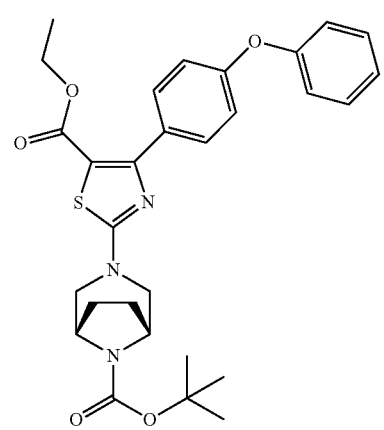 [SMILES: CCOC(=O)c1sc(N2C[C@H]3CC[C@@H](C2)N3C(=O)OC(C)(C)C)nc1-c1ccc(Oc2ccccc2)cc1] | I-14 | 536.34 |
| 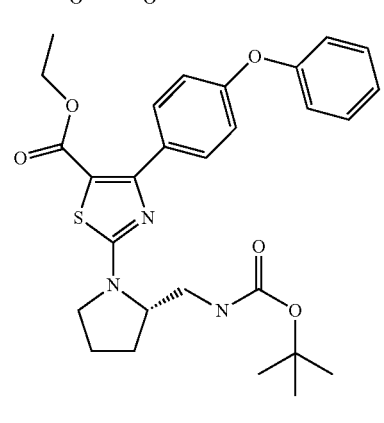 | I-15 | 495.61 |
| 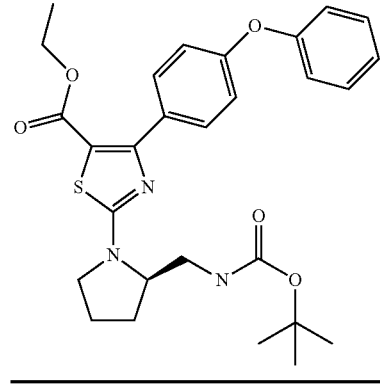 | I-16 | 495.37 |

44

Method 3

Synthesis of Intermediate 1-17

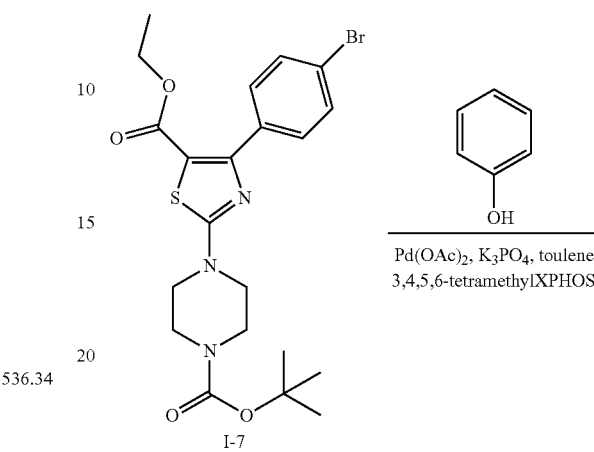

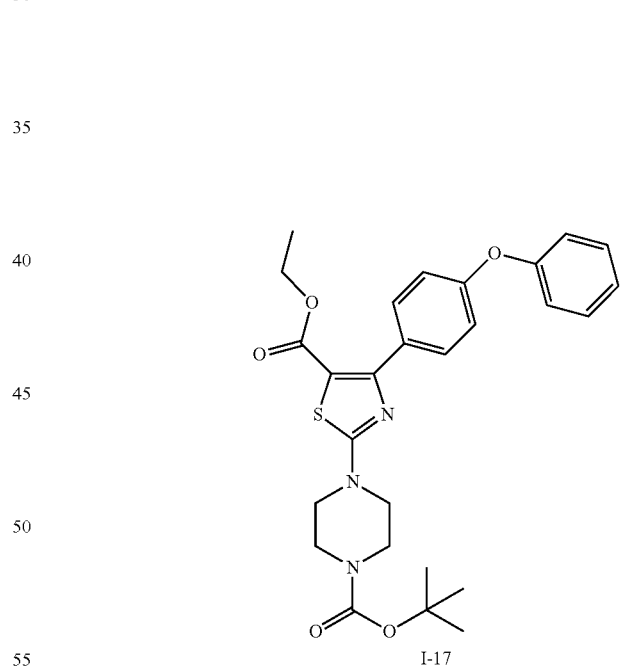

A mixture of 1-7 (0.5 g, 1.0 mmol), phenol (0.14 g, 1.5 mmol), Pd(OAc)$_2$ (0.011 g, 0.05 mmol), K$_3$PO$_4$ (0.43 g, 2.0 mmol) and 3,4,5,6-tetramethyl XPHOS in toleuen (1.5 mL) is placed in a seal tube with stirring. The reaction solution is degassed with Argon and heated to 110° C. for 1 hour. The reaction is then cooled to room temperature. The reaction solution is purified via Combi-flash column on silica gel (using a solvent gradient from 0-60% ethyl acetate in heptanes) to afford 1-17 (0.37 g, 72.1%), m/z 510.29 [M+H], RT 1.3 min.

The following intermediates were prepared in similar fashion:

| Structure | Intermediate | m/z |
|---|---|---|
| 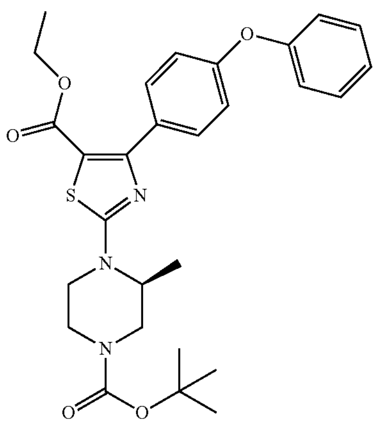 [SMILES: CCOC(=O)c1sc(N2CCN(C(=O)OC(C)(C)C)C[C@@H]2C)nc1-c1ccc(Oc2ccccc2)cc1] | I-18 | 524.33 |
| 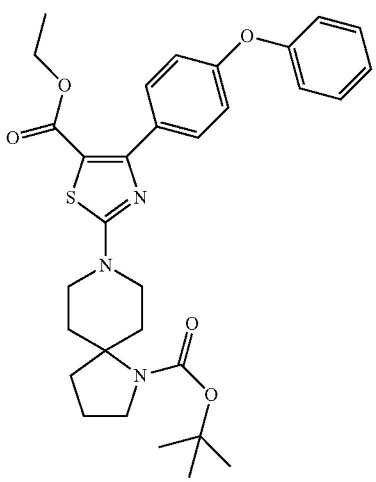 [SMILES: CCOC(=O)c1sc(N2CCC3(CCCN3C(=O)OC(C)(C)C)CC2)nc1-c1ccc(Oc2ccccc2)cc1] | I-19 | 564.40 |
| 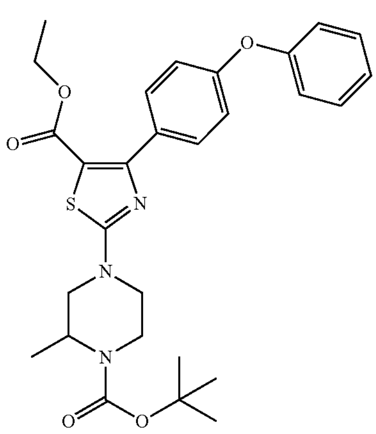 [SMILES: CCOC(=O)c1sc(N2CCN(C(=O)OC(C)(C)C)C(C)C2)nc1-c1ccc(Oc2ccccc2)cc1] | I-20 | 524.34 |

Method 4

Synthesis of Intermediate 1-21

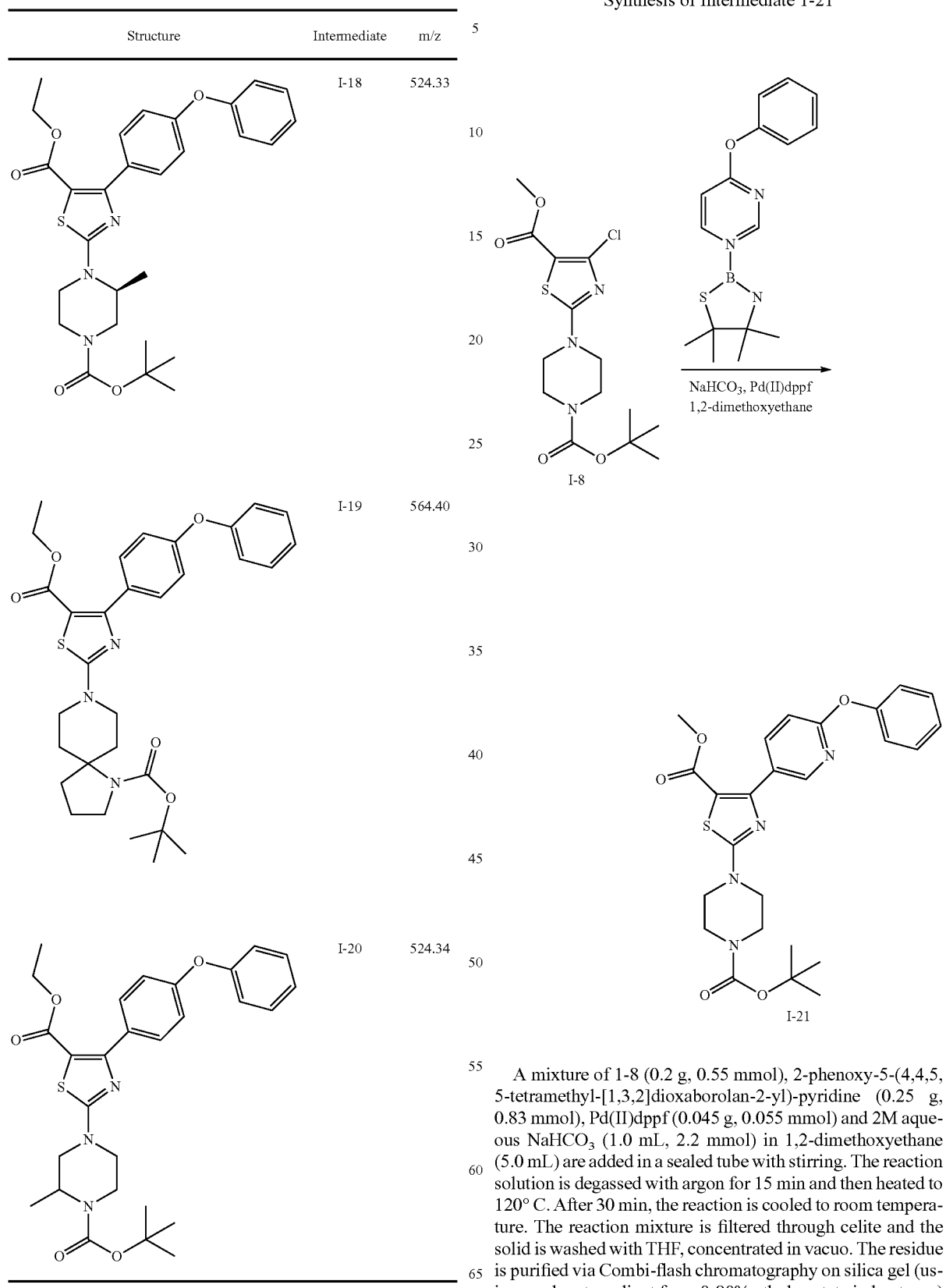

A mixture of 1-8 (0.2 g, 0.55 mmol), 2-phenoxy-5-(4,4,5,5-tetramethyl-[1,3,2]dioxaborolan-2-yl)-pyridine (0.25 g, 0.83 mmol), Pd(II)dppf (0.045 g, 0.055 mmol) and 2M aqueous NaHCO₃ (1.0 mL, 2.2 mmol) in 1,2-dimethoxyethane (5.0 mL) are added in a sealed tube with stirring. The reaction solution is degassed with argon for 15 min and then heated to 120° C. After 30 min, the reaction is cooled to room temperature. The reaction mixture is filtered through celite and the solid is washed with THF, concentrated in vacuo. The residue is purified via Combi-flash chromatography on silica gel (using a solvent gradient from 0-80% ethyl acetate in heptanes) to afford 1-21 (0.31 g, 100%), m/z 497.22 [M+H], RT 1.2 min 47
The following intermediate were prepared in similar fashion:
| Structure | Intermediate | m/z |
|---|---|---|
| 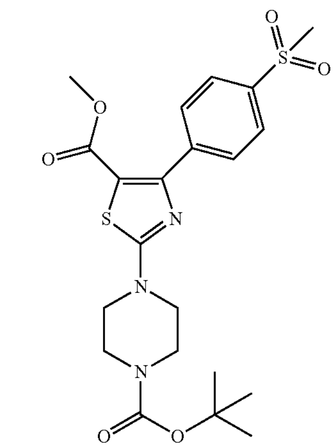 [SMILES: COC(=O)c1sc(N2CCN(C(=O)OC(C)(C)C)CC2)nc1-c1ccc(S(C)(=O)=O)cc1] | I-22 | N/A |
| 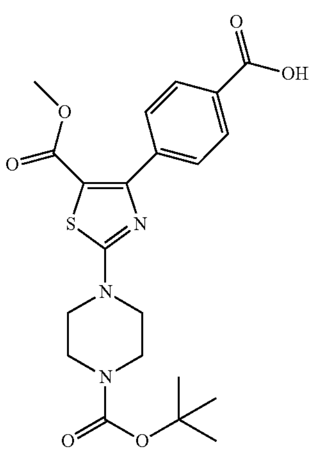 [SMILES: COC(=O)c1sc(N2CCN(C(=O)OC(C)(C)C)CC2)nc1-c1ccc(C(=O)O)cc1] | I-23 | N/A |
| 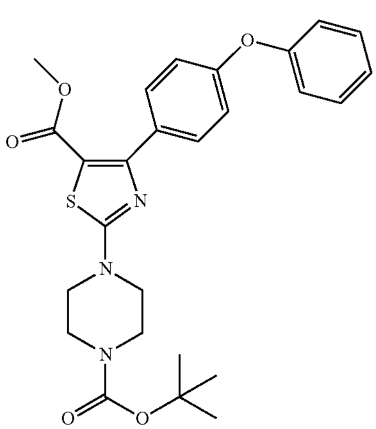 [SMILES: COC(=O)c1sc(N2CCN(C(=O)OC(C)(C)C)CC2)nc1-c1ccc(Oc2ccccc2)cc1] | I-24 | N/A |
-continued
| Structure | Intermediate | m/z |
|---|---|---|
| 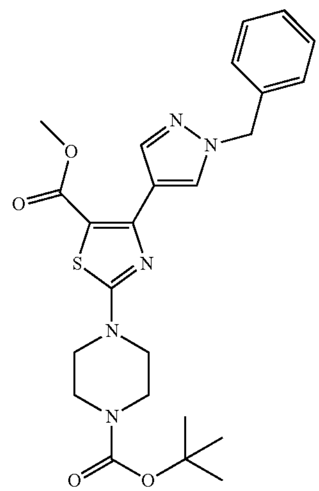 [SMILES: COC(=O)c1sc(N2CCN(C(=O)OC(C)(C)C)CC2)nc1-c1cnn(Cc2ccccc2)c1] | I-25 | N/A |
Method 5
Synthesis of Intermediate I-27
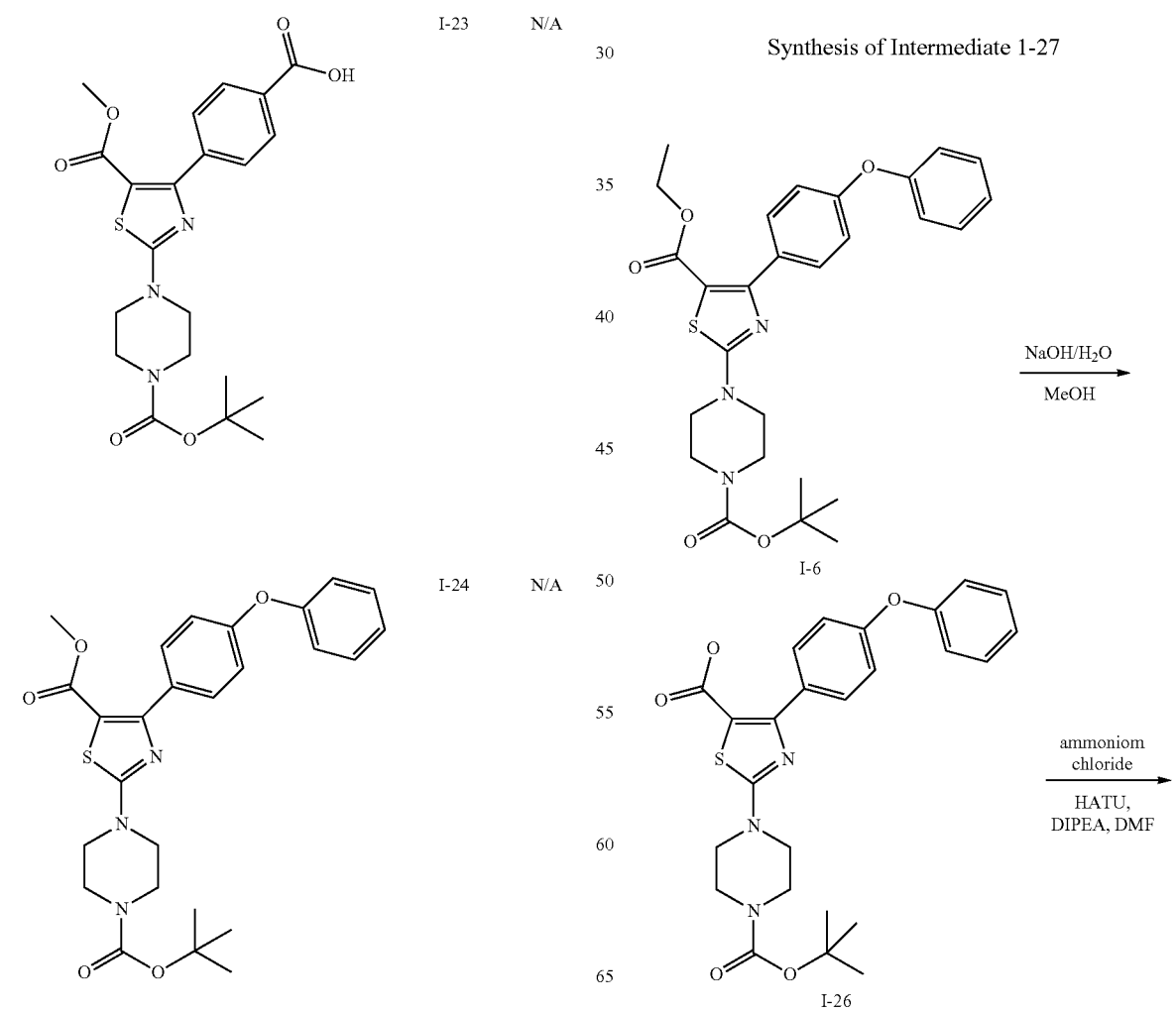

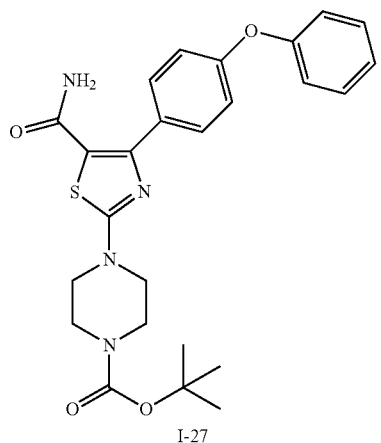

I-27

To a stirred solution of 1-6 (0.48 g, 1.0 mmol) in MeOH, 5.0 M aqueous NaOH (2.0 mL) is added. The reaction solution is heated to 60° C. After 1 hour, the reaction solution is acidified to pH=4 with concentrated aqueous HCl and concentrated in vacuo to afford I-26 (0.45 g, 100%) m/z 482.18 [M+H], RT 1.12 min.

To a stirred solution of I-26 (0.12 g, 0.25 mmol) in DMSO, HATU (0.2 g, 0.4 mmol) and di-isopropylethyl amine (0.13 mL, 0.75 mmol) is added at room temperature. After 20 mins, ammonium chloride (0.02 g, 0.4 mmol) is added to the reaction. The reaction solution is stirred for 1 hour and then concentrated in vacuo. The residue is purified via Combiflash chromatography on silica gel (using a solvent gradient from 0-70% ethyl acetate in heptanes) to afford I-27 (0.081 g, 67.6%) m/z 481.23 [M+H], RT 1.07 min The following intermediates were prepared in similar fashion:

| Structure | Intermediate | m/z |
|---|---|---|
| 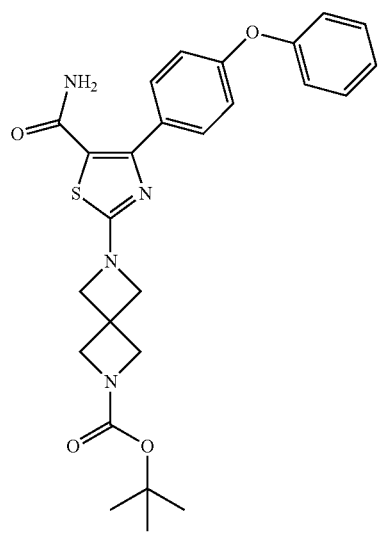 [SMILES: CC(C)(C)OC(=O)N1CC2(C1)CN(c1nc(-c3ccc(Oc4ccccc4)cc3)c(C(N)=O)s1)C2] | I-28 | 493.25 |
| 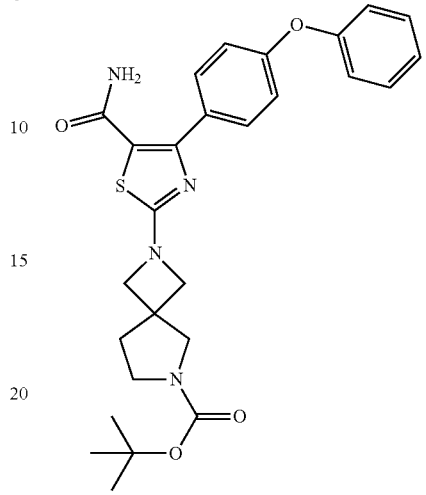 | I-29 | N/A |
| 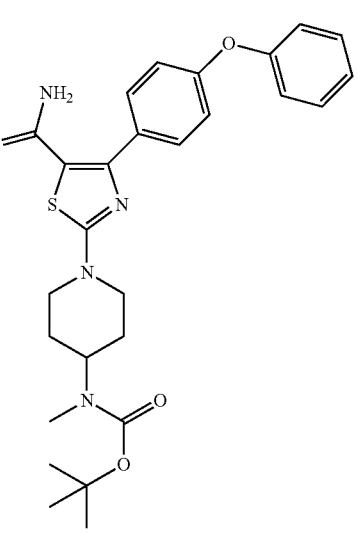 | I-30 | 509.29 |
| 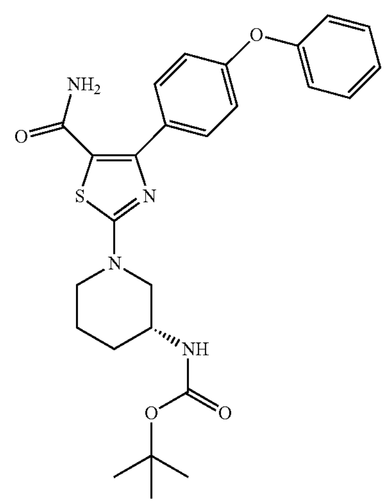 [SMILES: CC(C)(C)OC(=O)N[C@@H]1CCCN(c2nc(-c3ccc(Oc4ccccc4)cc3)c(C(N)=O)s2)C1] | I-31 | 496.23 |

| Structure | Intermediate | m/z |
|---|---|---|
| 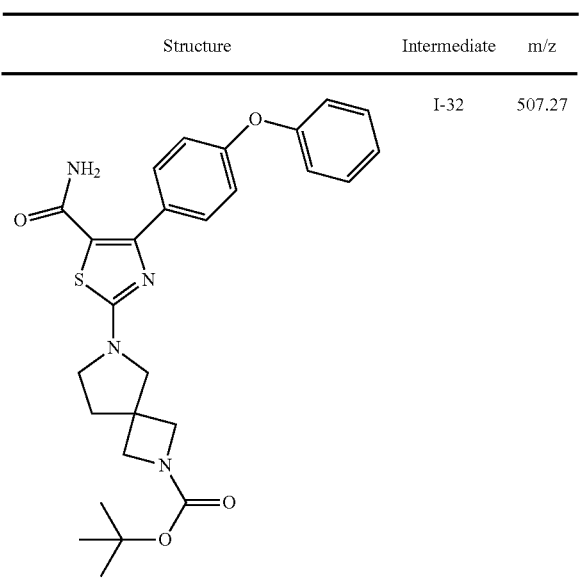 | I-32 | 507.27 |
| 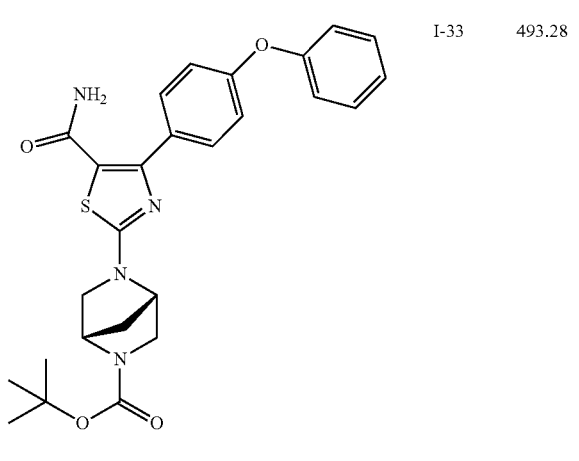 | I-33 | 493.28 |
| 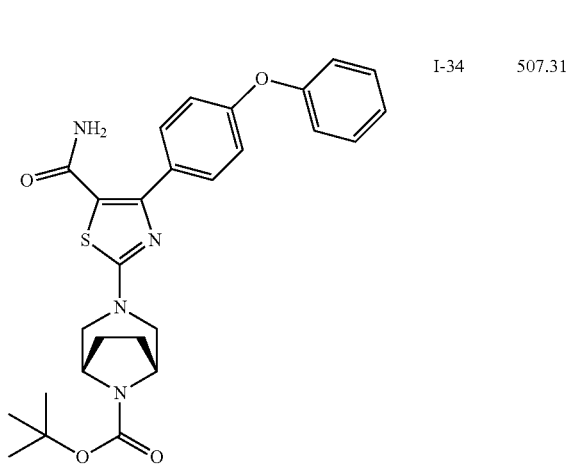 | I-34 | 507.31 |
| Structure | Intermediate | m/z |
|---|---|---|
| 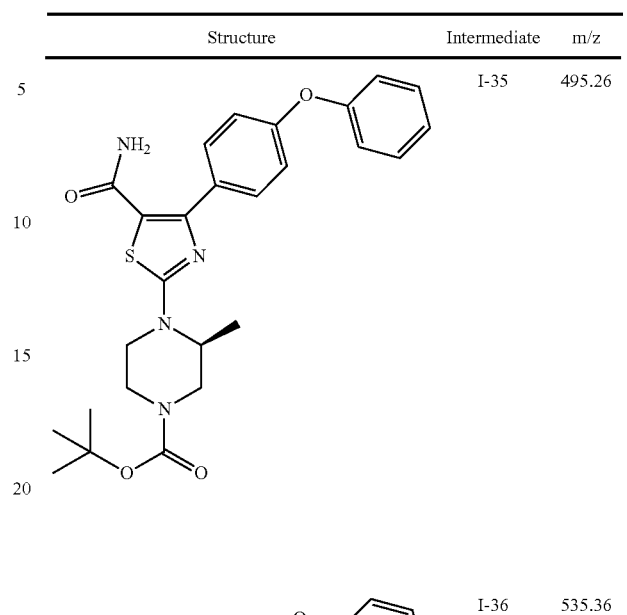 | I-35 | 495.26 |
| 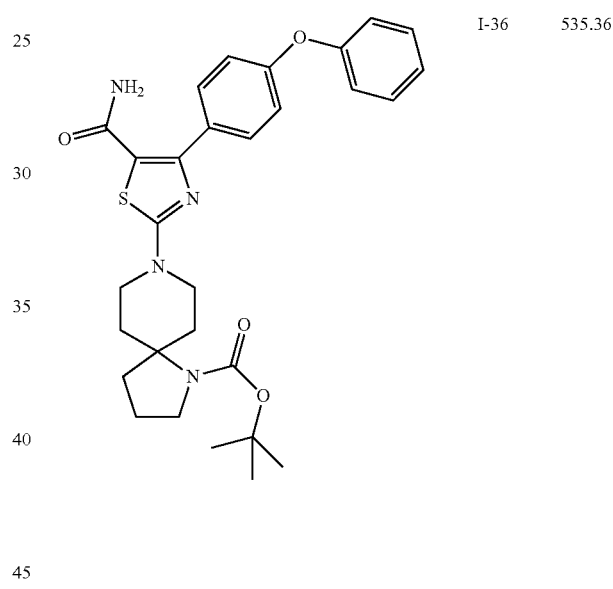 | I-36 | 535.36 |
| 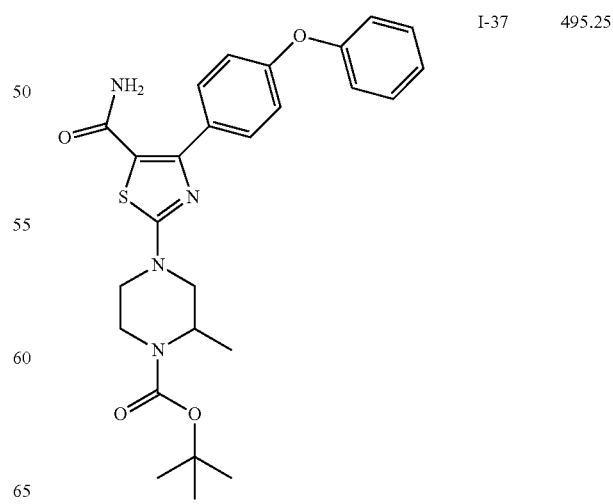 | I-37 | 495.25 |

| Structure | Intermediate | m/z |
|---|---|---|
| 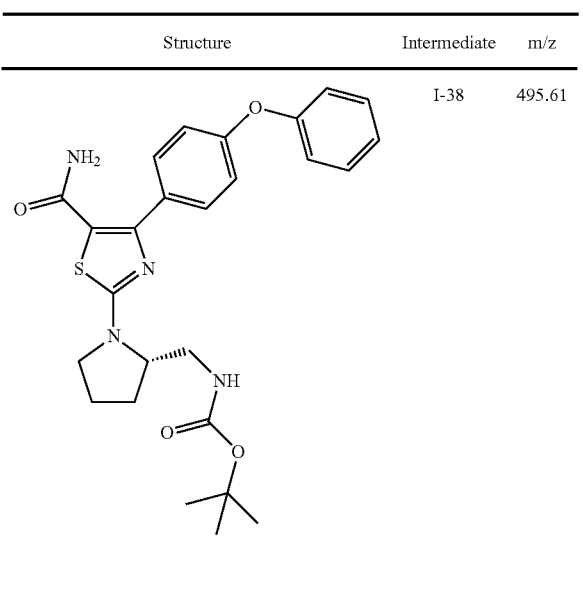 | I-38 | 495.61 |
| | I-39 | 495.37 |
| | I-40 | 469.24 |
| Structure | Intermediate | m/z |
|---|---|---|
| 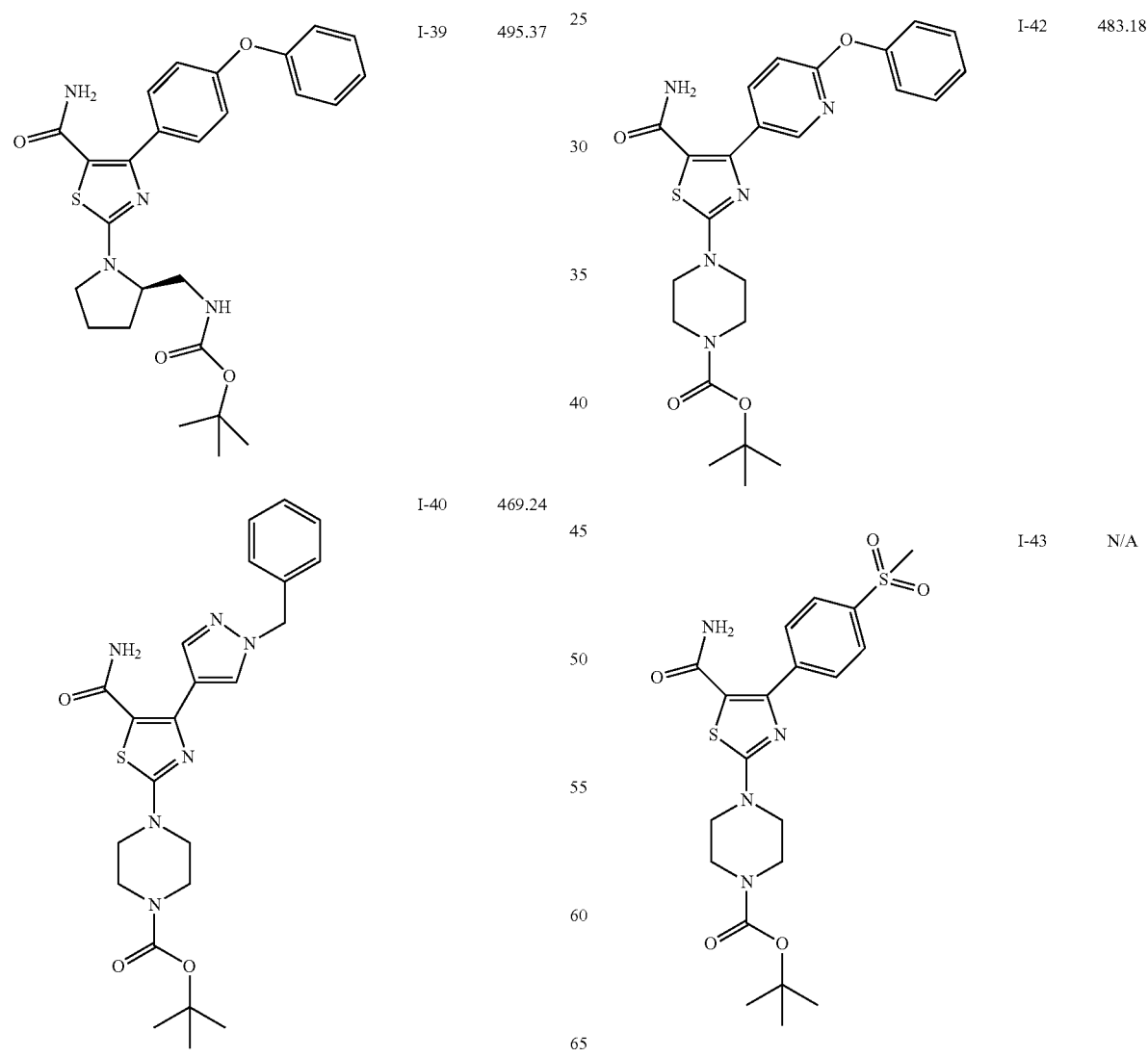 | I-41 | 467.12 |
| | I-42 | 483.18 |
| | I-43 | N/A |

55

-continued

| Structure | Intermediate | m/z |
|---|---|---|
| (structure) | I-44 | N/A |
| (structure) | I-45 | N/A |

Method 6

Synthesis of Example 12

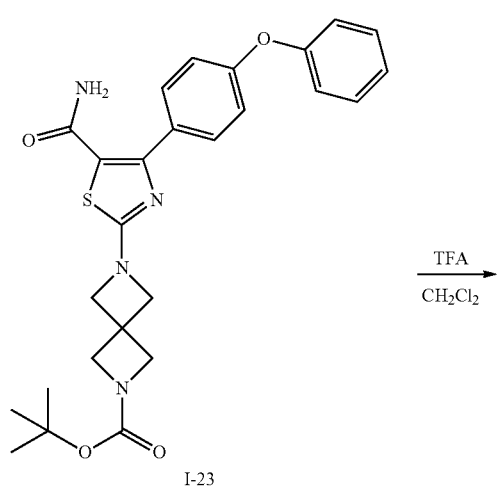

56

-continued

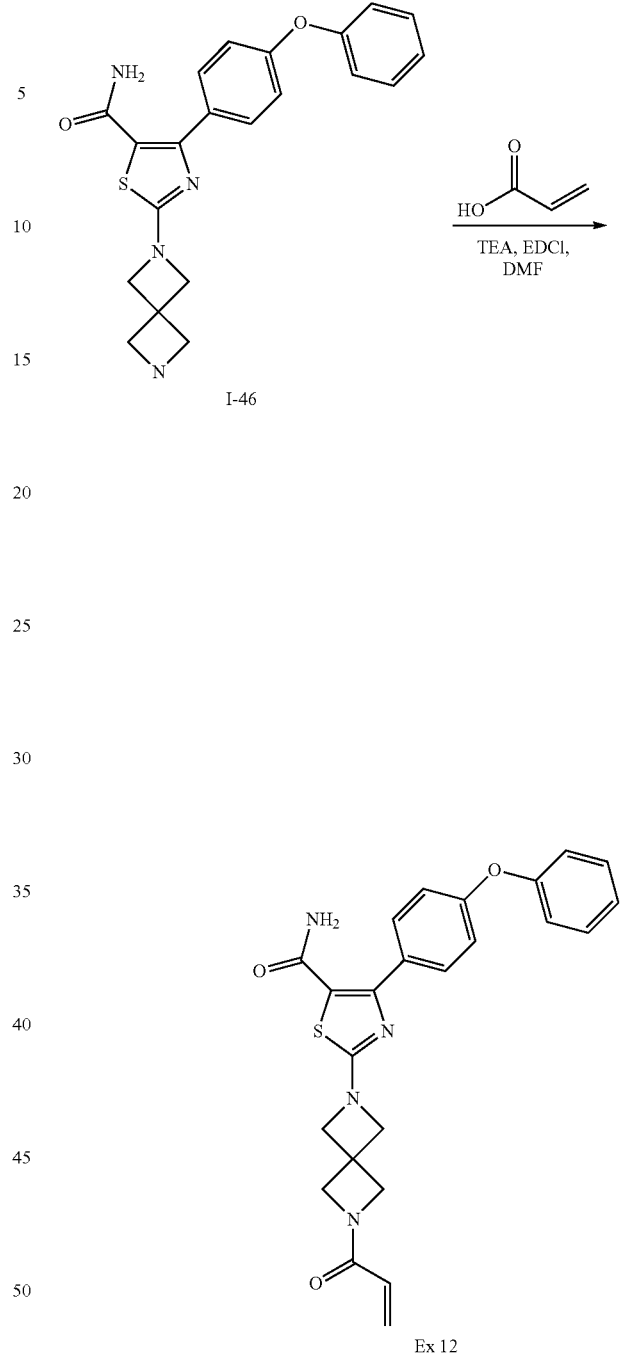

To a stirred solution of I-23 (0.92 g, 1.86 mmol) in $CH_2Cl_2$ is added TFA (1.0 mL, 12.9 mmol). After 3 hours, the reaction mixture was concentrated in vacuo. The residue was partioned between 10% MeOH in EtOAc and saturated aqueous $NaHCO_3$. The organic is collected, dried over sodium sulfate, filtered and concentrated in vacuo to afford I-46 (0.73 g, 100%).

To a stirred solution of I-46 (0.075 g, 0.15 mmol) in DMF, acrylic acid (0.015 mL, 0.22 mmol), EDCI (0.04 g, 0.22 mmol) and TEA (0.09 mL, 0.6 mmol) is added at room temperature. After 1 hour, the reaction solution is purified via prep-HPLC (waters CSH, 5-80% acetonitrile in water with 0.1% fromic acid) to afford Ex 12 (0.01 g, 15.1%) m/z 447.16 [M+H], RT 1.55 min Method 7

Synthesis of Example 7

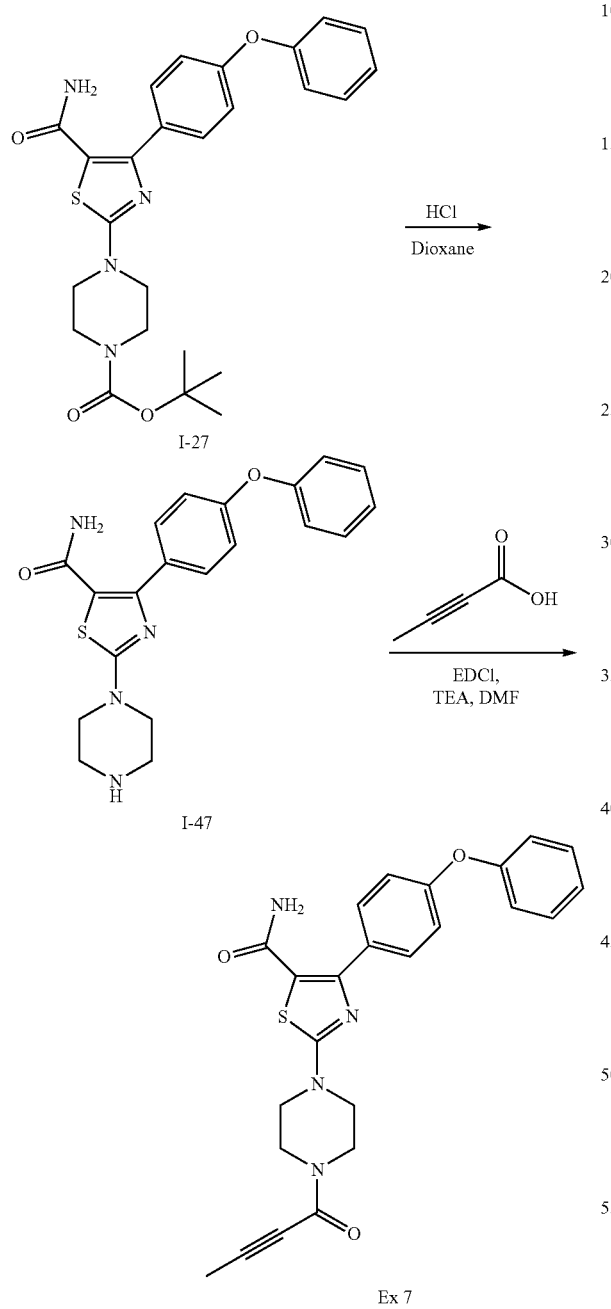

To a stirred solution of I-27 (0.12 g, 0.25 mmol) in dioxane, 4M HCl solution in dioxane is added. After 3 hours, the reaction solution is concentrated in vacuo to afford I-47 (0.1 g, 100%) m/z 381.381 [M+H], RT 0.62 min To a stirred solution of I-47 (0.04 g, 0.1 mmol) in DMF, But-2-ynoic acid (0.012 g, 0.15 mmol), EDCI (0.03 g, 0.15 mmol) and TEA (0.05 mL, 0.4 mmol) is added at room temperature. After 1 hour, the reaction solution is purified via Combi-flash chromatography on silica gel (using a solvent gradient from 0-7% MeOH in methylene chloride), followed by further purification via prep-HPLC (waters CSH, 5-80% acetonitrile in water with 0.1% fromic acid) to afford Ex 7 (0.014 g, 32.2%) m/z 447.16 [M+h], RT 2.12 min The following examples were prepared in similar fashion: Ex 1, 2, 3, 4, 5, 6, 7, 8, 9, 10, 11, 14, 16, 17, 18, 19, 21, 23, 24, 25, 26, 27, 28, 29, 30, 31, 32, 33, 34

Method 8

Synthesis of Example 22

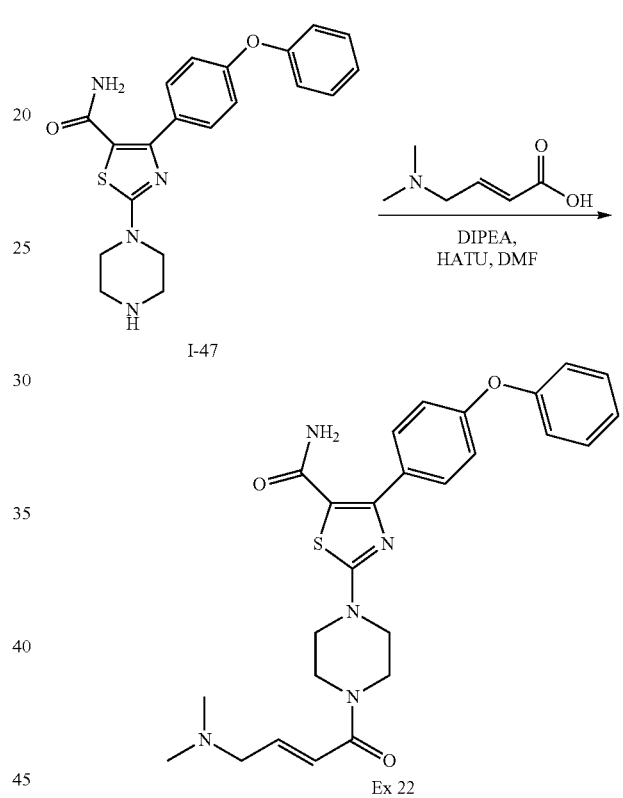

To a stirred solution of (E)-4-Dimethylamino-but-2-enoic acid (0.028 g, 0.22 mmol) in DMF is added HATU (0.082 g, 0.22 mmol). After 15 min, I-47 (0.05 g, 0.12 mmol) and DIPEA (0.084 mL, 0.48 mmol) are added to the solution. After 2 hours, the reaction solution was concentrated in vacuo. The residue is purified via prep-HPLC (CSH, 5-80% acetonitilre in water with 0.1% TFA) to afford Ex 22 (0.035 g, 59.4%, m/z 492.25 [M+H], RT 1.28 min)

The following examples were prepared in similar fashion: Ex 13, 15, 20, 22, 35, 36, 37, 38, 39, 40, 41, 42, 43, 44, 45, 46

Optimum reaction conditions and reaction times may vary depending on the particular reactants used. Unless otherwise specified, solvents, temperatures, pressures and other reaction conditions may be readily selected by one of ordinary skill in the art. Specific procedures are provided in the Synthetic Examples section. Intermediates and products may be purified by chromatography on silica gel, recrystallization and/or reverse phase HPLC (RHPLC). Discrete enantiomers may be obtained by resolution of racemic products using chiral HPLC. RHPLC purification methods used anywhere from 0-100% acetonitrile in water containing 0.1% formic acid or 0.1% TFA and used one of the following columns:
  a) Waters Sunfire OBD C18 5 µm 30×150 mm column
  b) Waters XBridge OBD C18 5 µm 30×150 mm column
  c) Waters ODB C8 5 µm 19×150 mm column
  d) Waters Atlantis ODB C18 5 µm 19×50 mm column.
  e) Waters Atlantis T3 OBD 5 µm 30×100 mm column
  f) Phenomenex Gemini Axia C18 5 µm 30×100 mm column HPLC Methods:
Analytical LC/MS Analysis Method A:
Column: Thermo Scientific, Aquasil C18, 50×2.1 mm, 5 µm column
Gradient:

| Time (min) | 0.1% Formic Acid in Water | 0.1% Formic Acid in CAN | Flow (ml/min) |
|---|---|---|---|
| 0 | 90 | 10 | 0.5 |
| 0.5 | 90 | 10 | 0.5 |
| 1.5 | 1 | 99 | 0.5 |
| 2.5 | 1 | 99 | 0.5 |
| 3.3 | 90 | 10 | 0.5 |
| 4.0 | 90 | 10 | 0.5 |

Analytical LC/MS Analysis Method B:
Column: Waters BEH 2.1×50 mm C18 1.7 µm column
Gradient:

| Time (min) | 95% Water/ 5% ACN (0.05% TFA) | ACN (0.05% TFA) | Flow (ml/min) |
|---|---|---|---|
| 0 | 90 | 10 | 0.8 |
| 1.19 | 0 | 100 | 0.8 |
| 1.7 | 0 | 100 | 0.8 |

The compounds according to the invention are prepared by the methods of synthesis described hereinafter in which the substituents of the general formulae have the meanings given hereinbefore. These methods are intended as an illustration of the invention without restricting its subject matter and the scope of the compounds claimed to these examples. Where the preparation of starting compounds is not described, they are commercially obtainable or may be prepared analogously to known compounds or methods described herein. Substances described in the literature are prepared according to the published methods of synthesis.

Compounds of formula I may be prepared as shown in Scheme Ia and Ib below.

Description of Biological Properties
BTK Assay

An HTRF assay (Cisbio KinEASE-TK cat #62TK0PEC) was performed to quantitate the ability of test compounds to inhibit BTK mediated phosphorylation of substrate. Assays were assembled in 384 well plates where 6 nM of full-length human His-tagged BTK (Life Technologies cat #PV3587) and test compound at varying concentrations were preincubated for 15 minutes at 28° C. Then, 1 uM of TK substrate-biotin and 30 uM ATP were added and incubated for an additional 30 minutes at 28° C. Phospohrylation was detected by adding 62.5 nM Streptavidin-XL665 and TK-Antibody Cryptate diluted 1:100 in HTRF detection buffer (Cisbio cat #62SDBRDF) and incubated for 60 minutes at RT. The plate was read on an Envision plate reader and the fluoresence is measured at 620 nm (cryptate) and 665 nm (XL665). A ratio is calculated (665/620) and converted to POC relative to control and blank wells.

Assay Buffer:
50 mM HEPES (Invitrogen #15630), 0.01% Brij-35 (sigma #B4184), 10 mM MgC12 (Sigma M1028), 1 mM EGTA (Ambion AM9262) and 100 uM sodium orthovanedate (Sigma S6508), 1 mM DTT (Sigma D5545) and 10 nM supplement enzyme buffer (Cisbio cat#61SEBALB).

Therapeutic Use

On the basis of their biological properties the compounds of formula (I) according to the invention, or their tautomers, racemates, enantiomers, diastereomers, mixtures thereof and the salts of all the above-mentioned forms are suitable for treating autoimmune and allergic disorders in that they exhibit good inhibitory effect upon BTK.

Such diseases include for example: rheumatoid arthritis, systemic lupus erythromatosis, scleroderma, asthma, allergic rhinitis, allergic eczema, B cell lymphoma, multiple sclerosis, juvenile rheumatoid arthritis, juvenile idiopathic arthritis, inflammatory bowel disease, graft versus host disease, psoriatic arthritis, ankylosing spondylitis and uveitis.

The compounds of formula (I) may be used on their own or in combination with other active substances according to the invention, optionally also in combination with other pharmacologically active substances.

Suitable preparations include for example tablets, capsules, suppositories, solutions—particularly solutions for injection (s.c., i.v., i.m.) and infusion—elixirs, emulsions or dispersible powders. The content of the pharmaceutically active compound(s) should be in the range from 0.1 to 90 wt.-%, preferably 0.5 to 50 wt.-% of the composition as a whole, i.e. in amounts which are sufficient to achieve the dosage range specified below. The doses specified may, if necessary, be given several times a day.

Suitable tablets may be obtained, for example, by mixing the active substance(s) with known excipients, for example inert diluents such as calcium carbonate, calcium phosphate or lactose, disintegrants such as corn starch or alginic acid, binders such as starch or gelatine, lubricants such as magnesium stearate or talc and/or agents for delaying release, to such as carboxymethyl cellulose, cellulose acetate phthalate, or polyvinyl acetate. The tablets may also comprise several layers.

Coated tablets may be prepared accordingly by coating cores produced analogously to the tablets with substances normally used for tablet coatings, for example collidone or shellac, gum arabic, talc, titanium dioxide or sugar. To achieve delayed release or prevent incompatibilities the core may also consist of a number of layers. Similarly the tablet coating may consist of a number of layers to achieve delayed release, possibly using the excipients mentioned above for the tablets.

Syrups or elixirs containing the active substances or combinations thereof according to the invention may additionally contain a sweetener such as saccharine, cyclamate, glycerol or sugar and a flavour enhancer, e.g. a flavouring such as vanillin or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates.

Solutions for injection and infusion are prepared in the usual way, e.g. with the addition of isotonic agents, preservatives such as p-hydroxybenzoates, or stabilisers such as alkali metal salts of ethylenediamine tetraacetic acid, optionally using emulsifiers and/or dispersants, whilst if water is used as the diluent, for example, organic solvents may optionally be used as solvating agents or dissolving aids, and transferred into injection vials or ampoules or infusion bottles.

Capsules containing one or more active substances or combinations of active substances may for example be prepared by mixing the active substances with inert carriers such as lactose or sorbitol and packing them into gelatine capsules.

Suitable suppositories may be made for example by mixing with carriers provided for this purpose such as neutral fats or polyethyleneglycol or the derivatives thereof.

Excipients which may be used include, for example, water, pharmaceutically acceptable organic solvents such as paraffins (e.g. petroleum fractions), vegetable oils (e.g. groundnut or sesame oil), mono- or polyfunctional alcohols (e.g. ethanol or glycerol), carriers such as e.g. natural mineral powders (e.g. kaolins, clays, talc, chalk), synthetic mineral powders (e.g. highly dispersed silicic acid and silicates), sugars (e.g. cane sugar, lactose and glucose), emulsifiers (e.g. lignin, spent sulphite liquors, methylcellulose, starch and polyvinylpyrrolidone) and lubricants (e.g. magnesium stearate, talc, stearic acid and sodium lauryl sulphate).

The preparations are administered by the usual methods, preferably by oral or transdermal route, most preferably by oral route. For oral administration the tablets may of course contain, apart from the above-mentioned carriers, additives such as sodium citrate, calcium carbonate and dicalcium phosphate together with various additives such as starch, preferably potato starch, gelatine and the like. Moreover, lubricants such as magnesium stearate, sodium lauryl sulphate and talc may be used at the same time for the tabletting process. In the case of aqueous suspensions the active substances may be combined with various flavour enhancers or colourings in addition to the excipients mentioned above.

For parenteral use, solutions of the active substances with suitable liquid carriers may be used.

The dosage for intravenous use is from 1-1000 mg per hour, preferably between 5 and 500 mg per hour.

However, it may sometimes be necessary to depart from the amounts specified, depending on the body weight, the route of administration, the individual response to the drug, the nature of its formulation and the time or interval over which the drug is administered. Thus, in some cases it may be sufficient to use less than the minimum dose given above, whereas in other cases the upper limit may have to be exceeded. When administering large amounts it may be advisable to divide them up into a number of smaller doses spread over the day.

All patent and non-patent documents or literature cited in this application are herein incorporated by reference in their entirety.

The invention claimed is:
1. A compound of the formula (I)

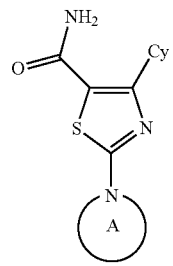
(I)

Cy is phenyl, pyrazolyl, pyridinyl, pyrrolyl, imidazolyl, thiazolyl, furanyl, oxazolyl, isoxazolyl, thienyl, pyridazinyl, pyrimidinyl, pyrazinyl or pyranyl each is substituted by $R_1$ and optionally substituted by halogen, halo $C_{1-4}$ alkyl, $C_{1-4}$ alkyl and $C_{1-4}$ alkoxy;

$R_1$ is chosen from:

L-Ar and —S(O)$_m$—R$_3$, each $R_1$ is optionally substituted by Br, $C_{1-4}$ alkyl, $R_3$—S(O)$_2$—, —CN, —C(O)—NH(R$_3$) and $C_{1-3}$ alkoxy;

L is a linker chosen from a bond, O, >C(O), —(CH$_2$)$_n$—, —O—(CH$_2$)$_n$—, —N(R$_3$)—, —N(R$_3$)—(CH$_2$)$_n$—, —(CH$_2$)$_n$—N(R$_3$)—, —C(O)—N(R$_3$)—, —C(O)—N(R$_3$)—(CH$_2$)$_n$—, —N(R$_3$)—C(O)—N(R$_3$)—, —N(R$_3$)—C(O)—, —S(O)$_m$—N(R$_3$)—, R$_3$—S(O)$_m$—, and —N(R$_3$)—S(O)$_m$—, wherein the —CH$_2$— in each L can have 1-2 hydrogens replaced by $C_{1-3}$ alkyl, said $C_{1-3}$ alkyl groups can optionally cyclize to form a $C_{3-6}$ cycloalkyl ring;

Ar is phenyl, pyridinyl, pyridazinyl, pyrimidinyl, pyrazinyl, benzoxazolyl, indolyl, isoindolyl, benzofuranyl, benzimidazolyl, benzothiazolyl, piperidinyl, piperazinyl or pyrrolidinyl;

Ring A of the formula (I) is an N-linked heterocycle chosen from $C_5$-$C_{10}$ spirocycle and a nitrogen containing optionally bridged mono- or bi-cyclic heterocycle, each Ring A is substituted by one Y and optionally substituted by halogen, halo $C_{1-4}$ alkyl, $C_{1-4}$ alkyl and $C_{1-4}$ alkoxy;

Y is —(CH$_2$)$_n$—N(R$_3$)—R$_4$, or Y is R$_4$;

$R_4$ is

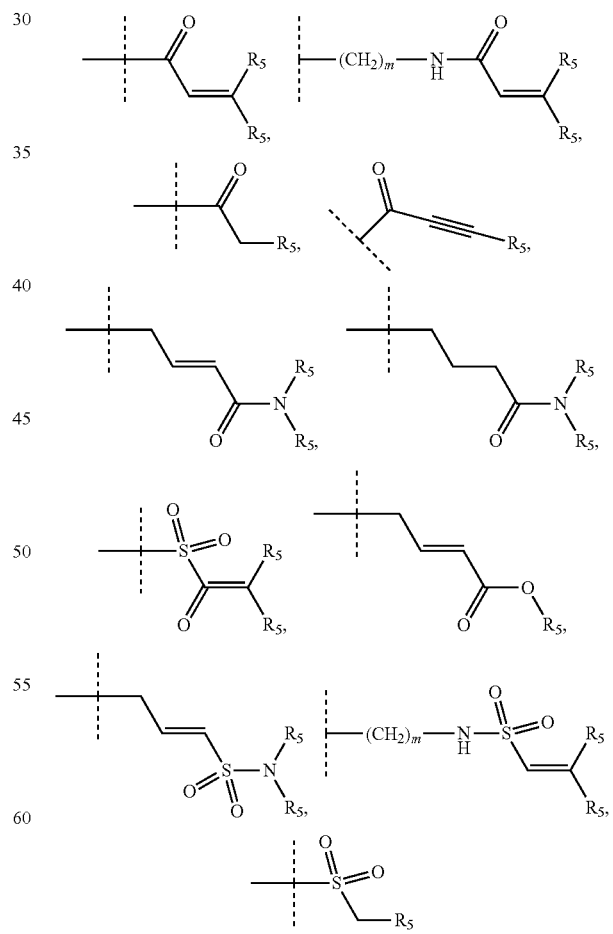

wherein R₅ cannot be hydrogen

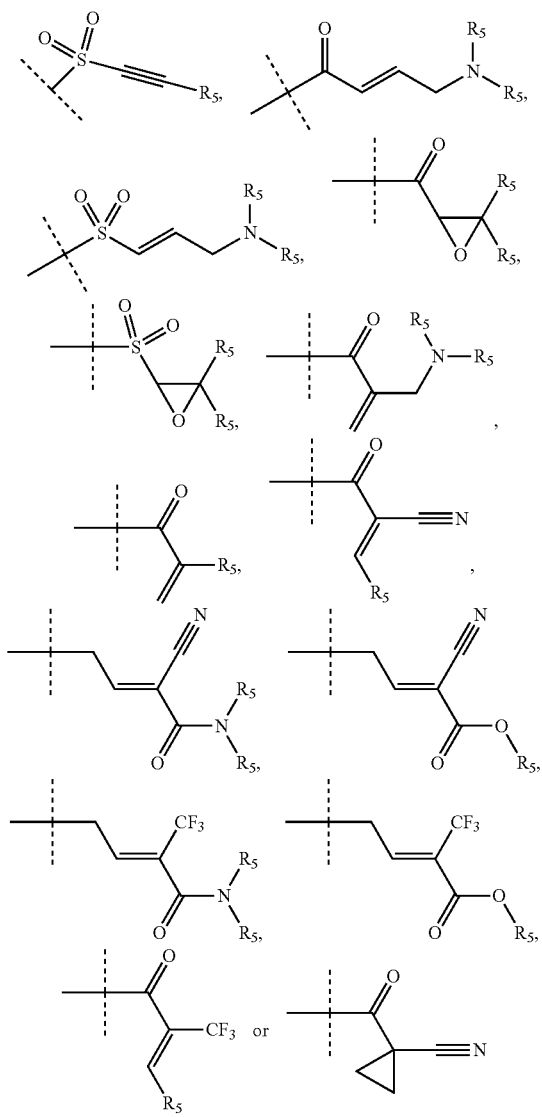

each n is independently 1-4;
each m is independently 0-2;
each R₂ and R₃ are independently chosen from hydrogen or C_{1-4} alkyl;
each R₅ is independently chosen from hydrogen, halogen, C_{1-4} alkyl, C_{1-4} alkoxy, C_{1-4} alkylC_{1-4}alkoxy, C_{1-4}alkylhydroxy, —(CH₂)_n-heterocycle and heterocycle each heterocycle optionally substituted by halogen, OH or R₂—S(O)_m—;
each group defined above for Cy, R₁—R₅, and Y can be where possible partially or fully halogenated;
or a pharmaceutically acceptable salt thereof.

2. The compound according to claim 1 wherein
Cy is substituted by R₁ and optionally substituted by F, Cl or C_{1-4} alkoxy;
or a pharmaceutically acceptable salt thereof.

3. The compound according to claim 2 wherein
Cy is phenyl, pyrazolyl or pyridinyl, each is substituted by R₁ and optionally substituted by F, Cl or C_{1-2} alkoxy;

R₁ is L-Ar, each R₁ is optionally substituted by Br, C_{1-4} alkyl, CH₃—S(O)₂—, —CN, —C(O)—NH(R₃) and C_{1-2} alkoxy;
Ar is phenyl, pyridinyl, pyridazinyl, pyrimidinyl, pyrazinyl, benzoxazolyl, indolyl, isoindolyl, benzofuranyl, benzimidazolyl, benzothiazolyl or piperidinyl or a pharmaceutically acceptable salt thereof.

4. The compound according to claim 3 wherein
Cy is phenyl or pyridinyl, each is substituted by R₁ and optionally substituted by F, Cl or C_{1-2} alkoxy;
L-Ar is optionally substituted by F, Cl, C_{1-4} alkyl, CH₃—S(O)₂—, —CN, —C(O)—NH(CH₃) and C_{1-2} alkoxy;
Ar is phenyl or pyridinyl;
or a pharmaceutically acceptable salt thereof.

5. The compound according to claim 4 wherein
Ring A is an N-linked heterocycle chosen from:
a spirocycle chosen from

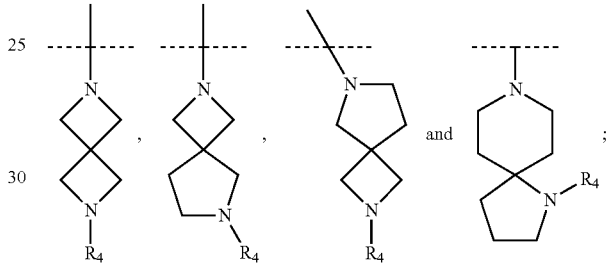

each Ring A is substituted by one Y and optionally substituted by halogen or C_{1-4} alkyl;
or a pharmaceutically acceptable salt thereof.

6. The compound according to claim 3 wherein
Ring A is chosen from:

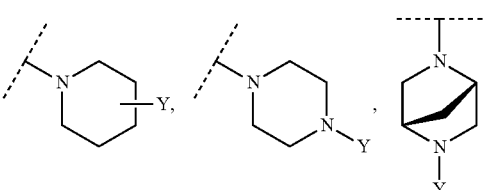

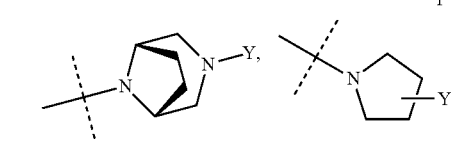

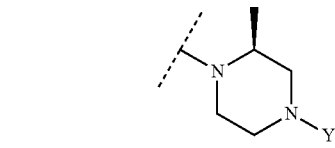

each Ring A is substituted by one Y and optionally substituted by halogen or C_{1-4} alkyl;
or a pharmaceutically acceptable salt thereof.

7. The compound according to claim 6 wherein R₄ is;

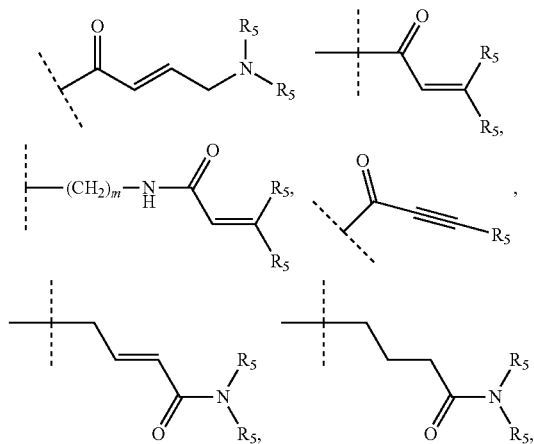

each R₅ is independently chosen from hydrogen, C₁₋₃ alkyl, halo C₁₋₃ alkyl, C₁₋₃ alkylC₁₋₃ alkoxy, —CH₂-heterocycle and heterocycle each heterocycle optionally substituted by F, Cl, OH and CH₃—S(O)₂— and each heterocycle chosen from pyrrolidinyl, piperidinyl, morpholinyl and 1,4-oxazepane, or a pharmaceutically acceptable salt thereof.

8. The compound according to claim 7 wherein
L is a linker chosen from a bond, O, —CH₂—, —C(O)—NH—, —NH—C(O)— and R₃—S(O)ₘ—;
or a pharmaceutically acceptable salt thereof.

9. The compound according to claim 8 wherein
L is a linker chosen from a bond, O and —CH₂—;
or a pharmaceutically acceptable salt thereof.

10. The compound according to claim 3 wherein
Cy is

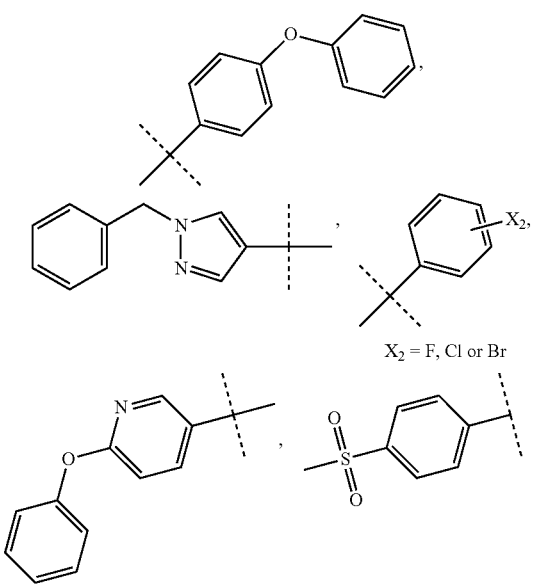

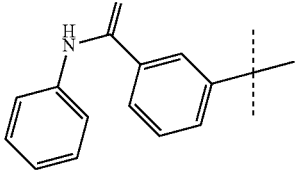

or a pharmaceutically acceptable salt thereof.

11. The compound according to claim 9 wherein
Cy is

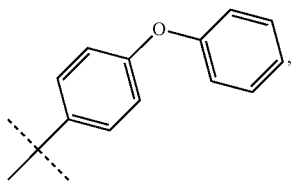

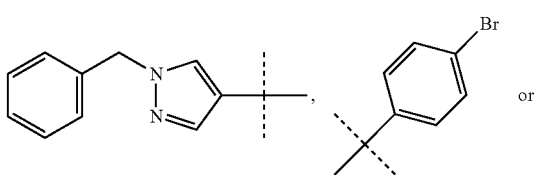

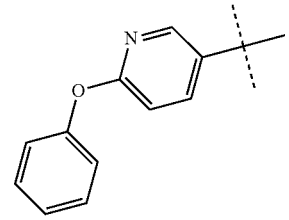

or a pharmaceutically acceptable salt thereof.

12. The compound according to claim 1 wherein Ring A is

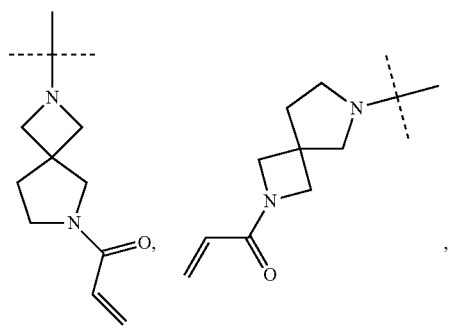

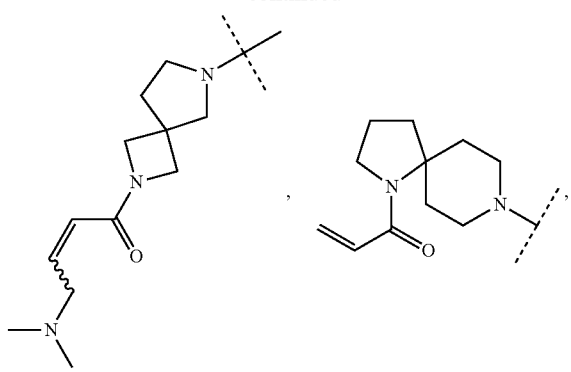
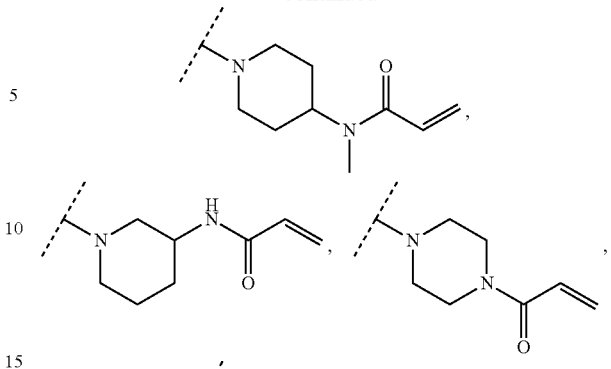

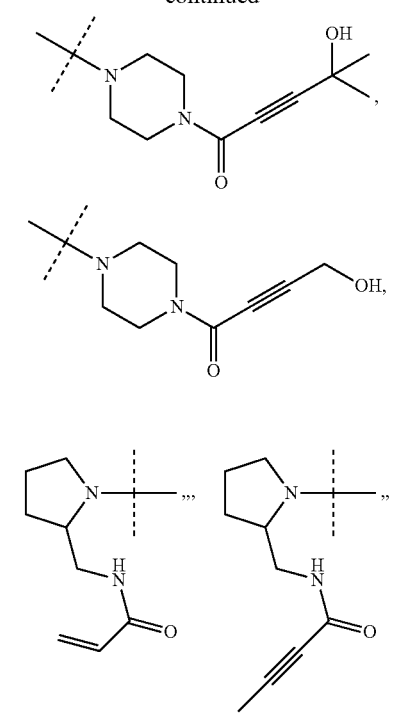
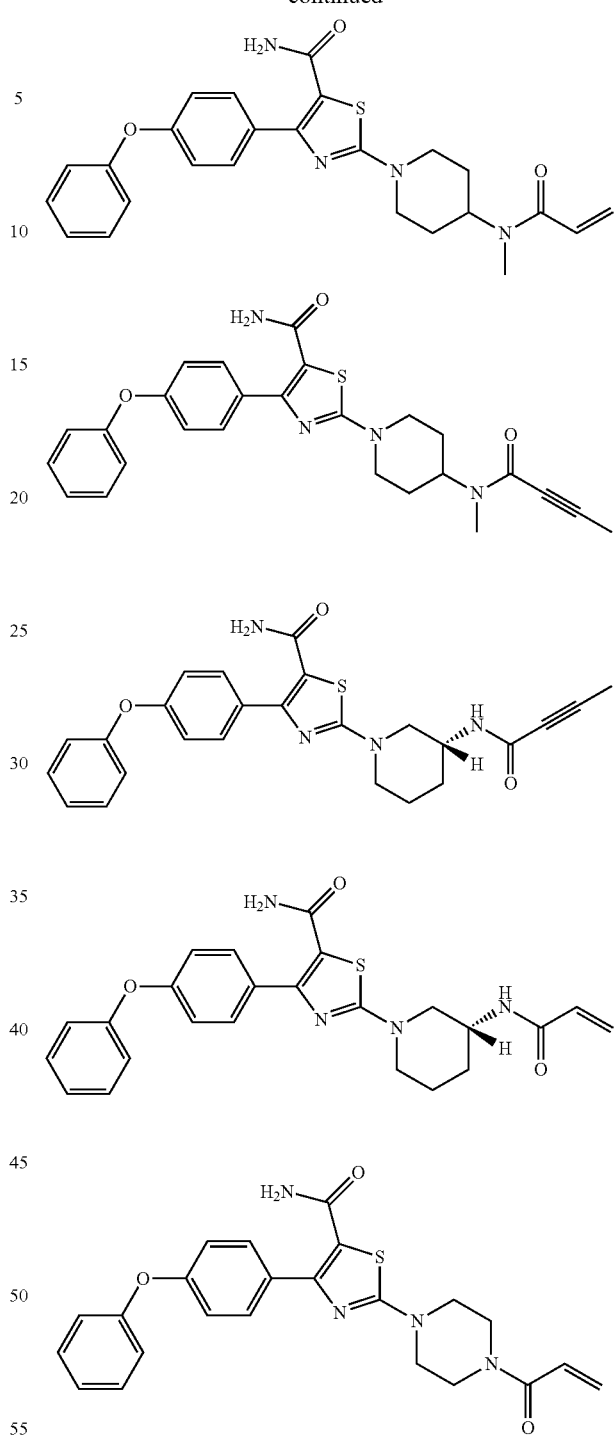
or a pharmaceutically acceptable salt thereof.
13. A compound chosen from
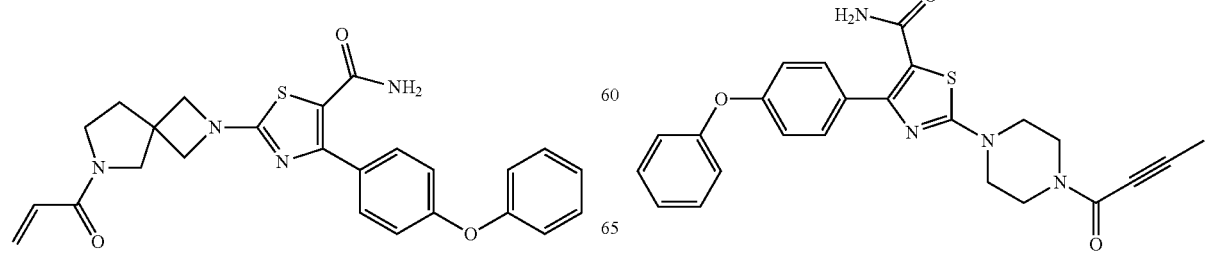

71
-continued
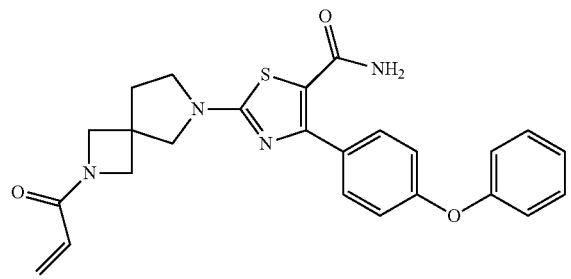
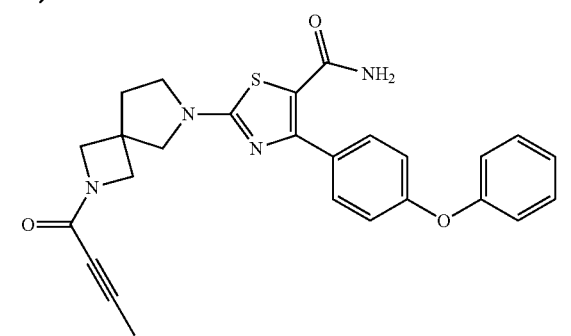
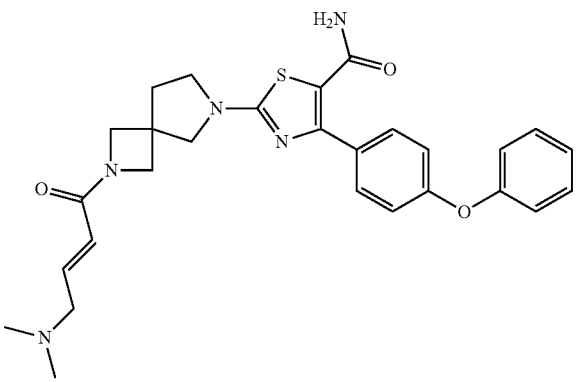
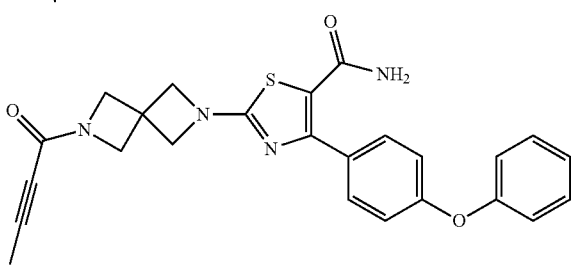
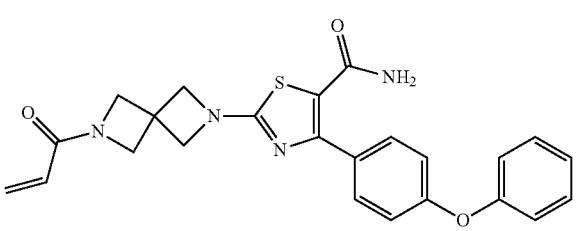
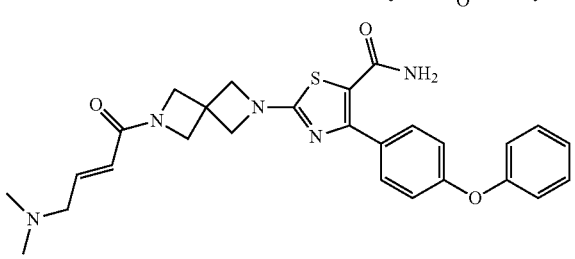
72
-continued
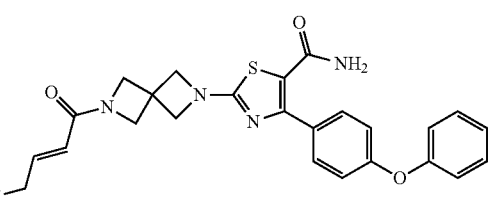
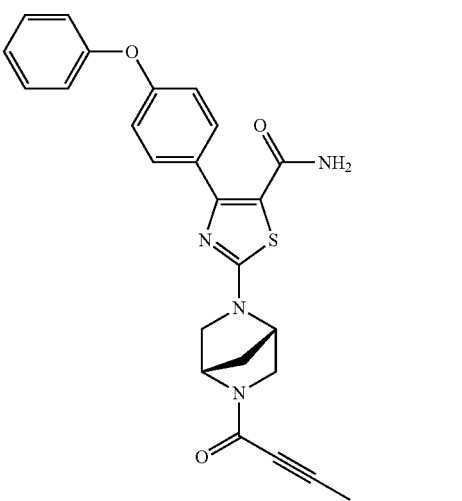
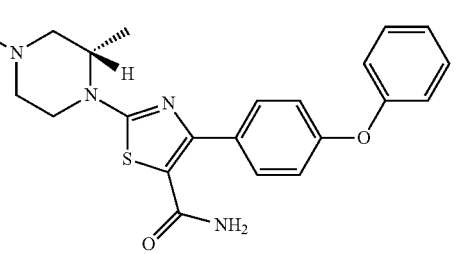
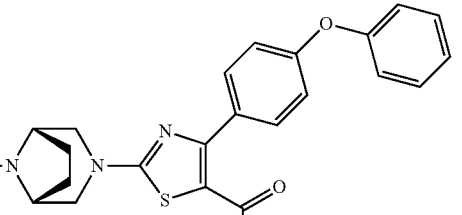

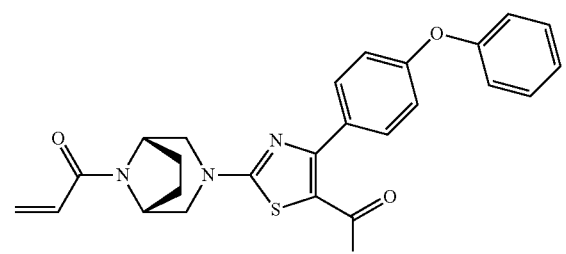
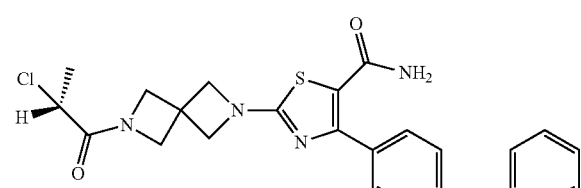
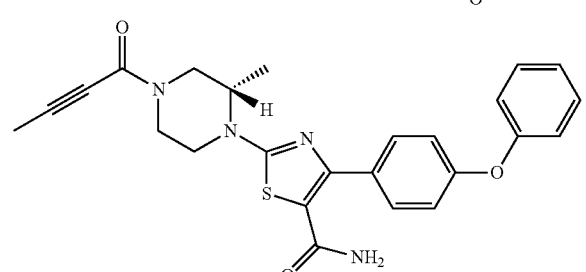
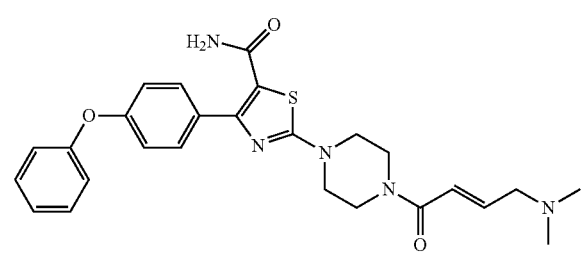
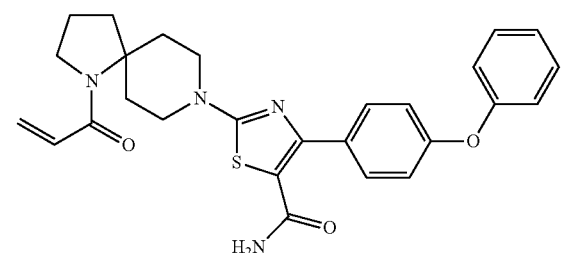
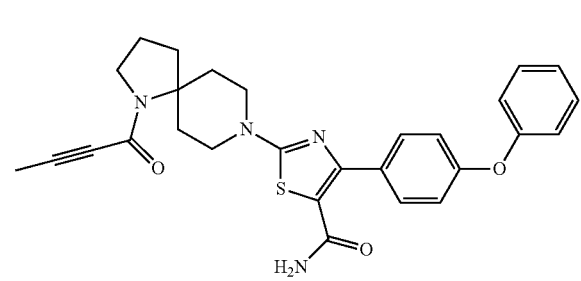
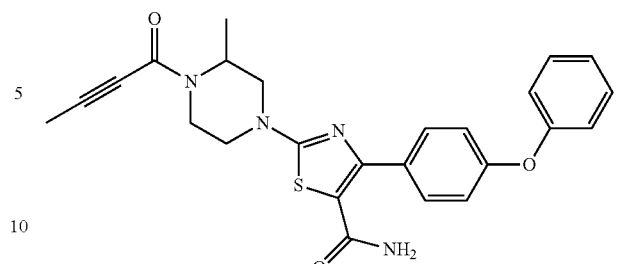
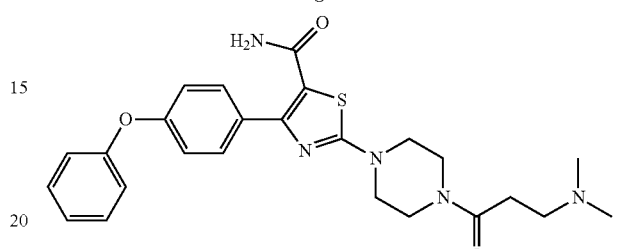
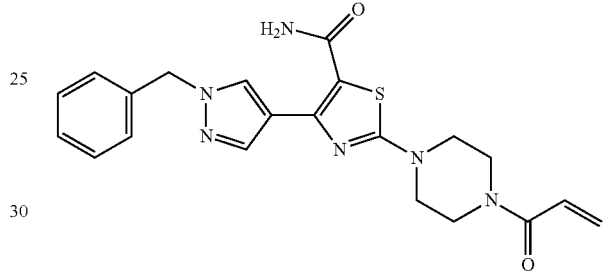
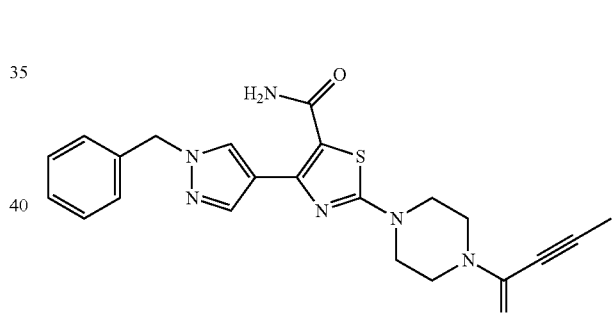
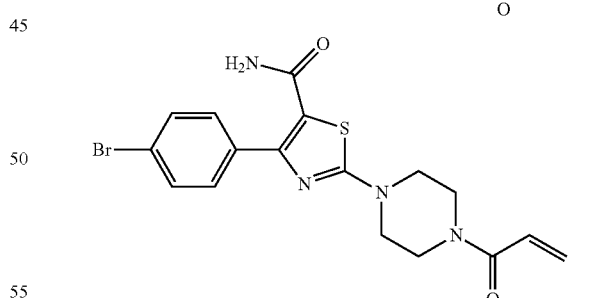
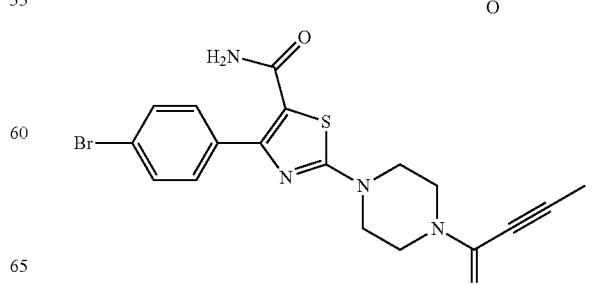

75
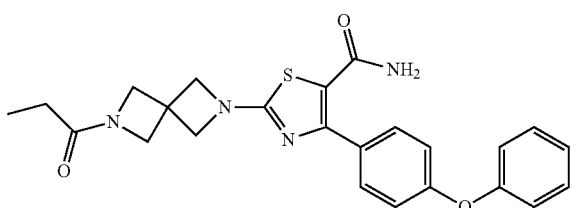
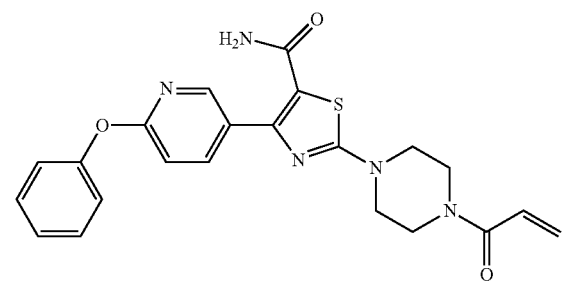
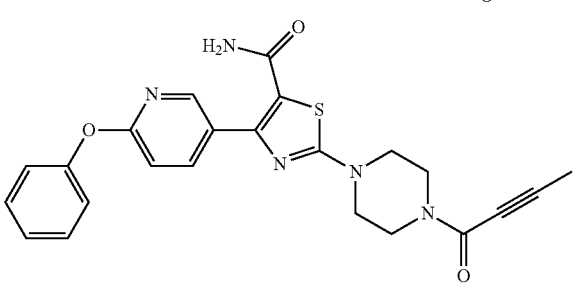
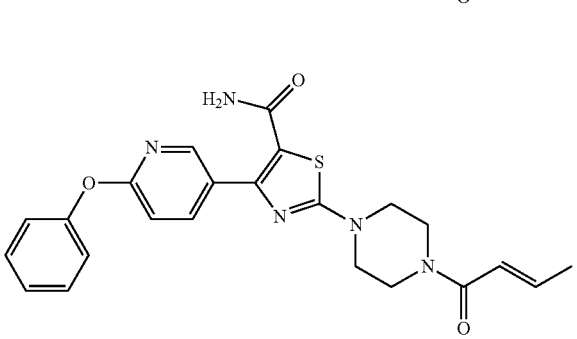
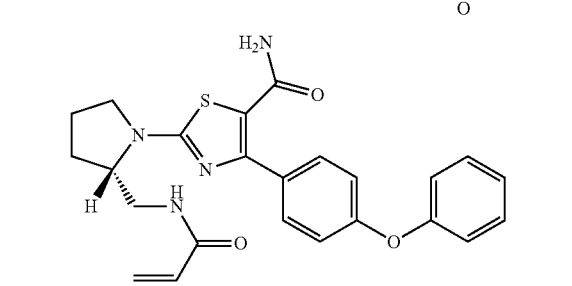
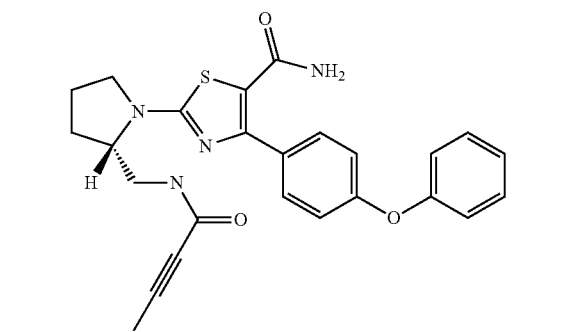
76
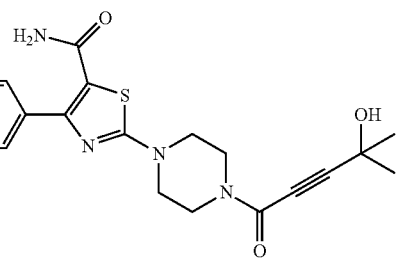
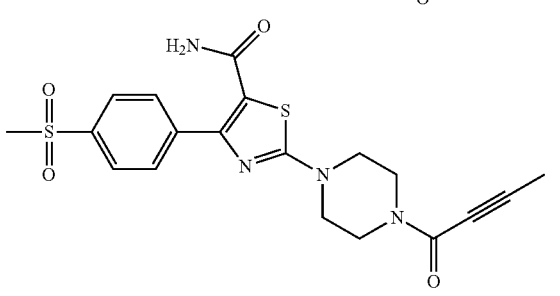
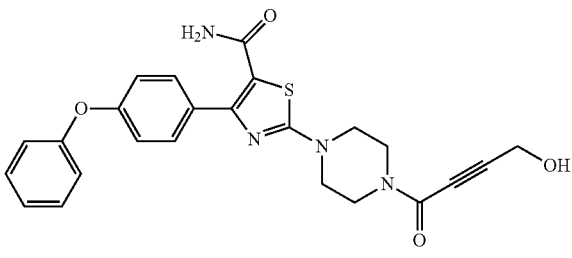
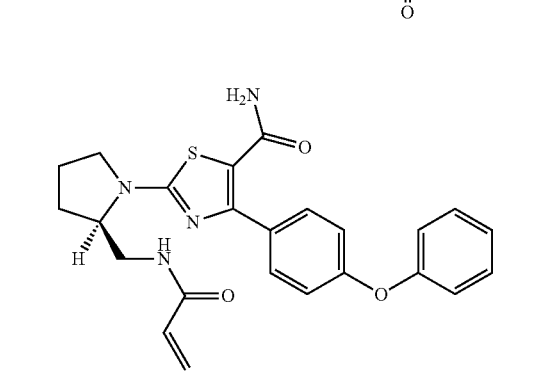
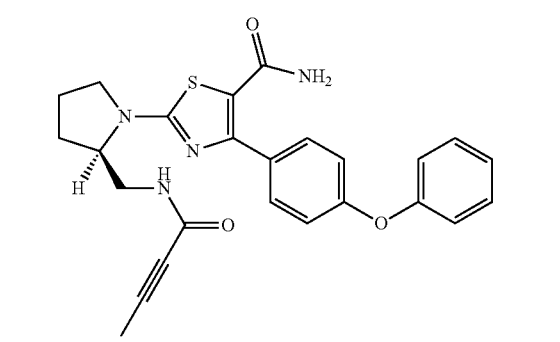
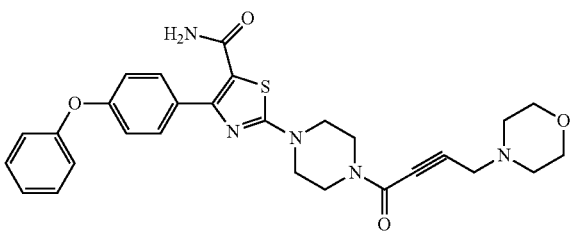

-continued

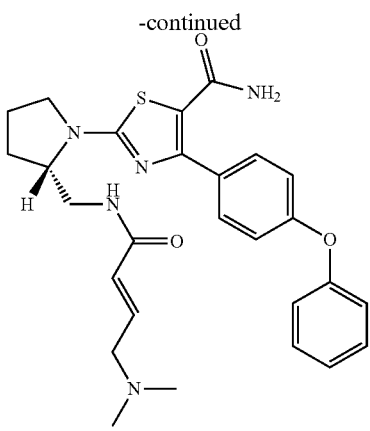

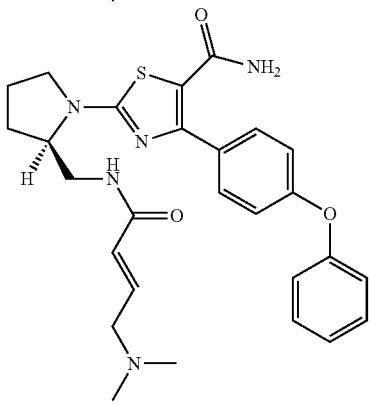

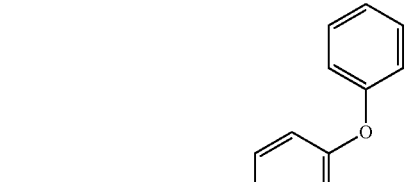

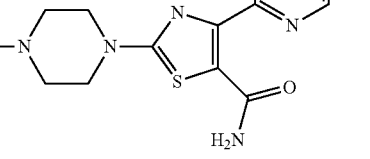

and

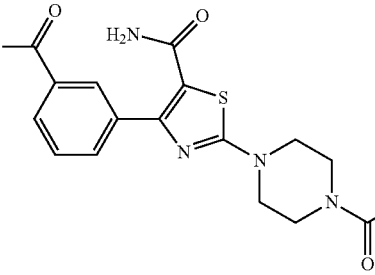

or a pharmaceutically acceptable salt thereof.

14. A pharmaceutical composition comprising a therapeutically effective amount of a compound according to claim 1 or a pharmaceutically acceptable salt thereof.

15. A method of treating a disease chosen from rheumatoid arthritis, systemic lupus erythromatosis, scleroderma, asthma, allergic rhinitis, allergic eczema, B cell lymphoma, multiple sclerosis, juvenile rheumatoid arthritis, juvenile idiopathic arthritis, inflammatory bowel disease, graft versus host disease, psoriatic arthritis, ankylosing spondylitis and uveitis, comprising administering to a patient a therapeutically effective amount of a compound according to claim 1 or a pharmaceutically acceptable salt thereof.

16. A compound of the formula (I)

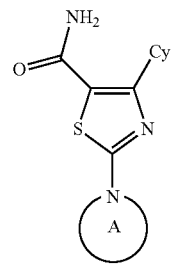

Cy is phenyl, pyrazolyl, pyridinyl, pyrrolyl, imidazolyl, thiazolyl, furanyl, oxazolyl, isoxazolyl, thienyl, pyridazinyl, pyrimidinyl, pyrazinyl or pyranyl each is substituted by $R_1$ and optionally substituted by halogen, halo $C_{1-4}$ alkyl, $C_{1-4}$ alkyl and $C_{1-4}$ alkoxy;

$R_1$ is chosen from:

L-Ar and —S(O)$_m$—$R_3$, each $R_1$ is optionally substituted by Br, $C_{1-4}$ alkyl, $R_3$—S(O)$_2$—, —CN, —C(O)—NH($R_3$) and $C_{1-3}$ alkoxy;

L is a linker chosen from a bond, O, >C(O), —(CH$_2$)$_n$—, —O—(CH$_2$)$_n$—, —N(R$_3$)—, —N(R$_3$)—(CH$_2$)$_n$—, —(CH$_2$)$_n$—N(R$_3$)—, —C(O)—N(R$_3$)—, —C(O)—N(R$_3$)—(CH$_2$)$_n$—, —N(R$_3$)—C(O)—N(R$_3$)—, —N(R$_3$)—C(O)—, —S(O)$_m$—N(R$_3$)—, $R_3$—S(O)$_m$—, and —N(R$_3$)—S(O)$_m$—, wherein the —CH$_2$— in each L can have 1-2 hydrogens replaced by $C_{1-3}$ alkyl, said $C_{1-3}$ alkyl groups can optionally cyclize to form a $C_{3-6}$ cycloalkyl ring;

Ar is phenyl, pyridinyl, pyridazinyl, pyrimidinyl, pyrazinyl, benzoxazolyl, indolyl, isoindolyl, benzofuranyl, benzimidazolyl, benzothiazolyl, piperidinyl, piperazinyl or pyrrolidinyl;

Ring A of the formula (I) is

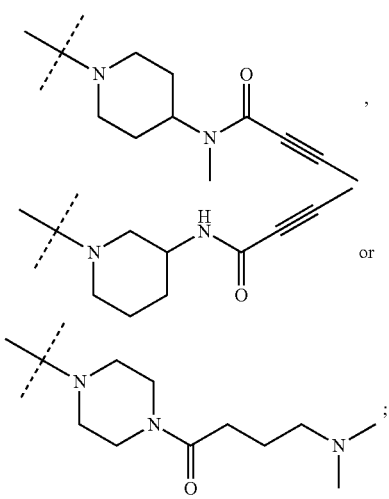

each n is independently 1-4;
each m is independently 0-2;
$R_3$ is independently chosen from hydrogen or $C_{1-4}$ alkyl;
each group defined above for Cy, $R_1$ and $R_3$ can be where possible partially or fully halogenated;
or a pharmaceutically acceptable salt thereof.

* * * * *